(12) United States Patent
Refvik

(10) Patent No.: US 9,980,671 B2
(45) Date of Patent: May 29, 2018

(54) SYSTEMS AND METHODS FOR MANAGEMENT OF MEDICAL CONDITION

(71) Applicant: Johnnie J. Refvik, Newport Beach, CA (US)

(72) Inventor: Johnnie J. Refvik, Newport Beach, CA (US)

( * ) Notice: Subject to any disclaimer, the term of this patent is extended or adjusted under 35 U.S.C. 154(b) by 56 days.

(21) Appl. No.: 14/217,385

(22) Filed: Mar. 17, 2014

(65) Prior Publication Data
US 2014/0380218 A1    Dec. 25, 2014

Related U.S. Application Data

(60) Provisional application No. 61/790,453, filed on Mar. 15, 2013, provisional application No. 61/790,583, (Continued)

(51) Int. Cl.
G06F 3/048        (2013.01)
A61B 5/15         (2006.01)
(Continued)

(52) U.S. Cl.
CPC ...... *A61B 5/150305* (2013.01); *A61B 5/0022* (2013.01); *A61B 5/14532* (2013.01); *A61B 5/151* (2013.01); *A61B 5/157* (2013.01); *A61B 5/150022* (2013.01); *A61B 5/15146* (2013.01); *A61B 5/15186* (2013.01); *A61B 5/150267* (2013.01); *A61B 5/150358* (2013.01); *A61B 5/6898* (2013.01); *A61B 5/7445* (2013.01); *A61M 5/3155* (2013.01); *G01N 33/66* (2013.01); *G06F 3/0488* (2013.01); *G06F 3/04817* (2013.01); *G06F 3/04842* (2013.01);
(Continued)

(58) Field of Classification Search
CPC ............. G06F 19/3406; G06F 3/04842; G06F 3/04817; G06F 3/0488
USPC .................................................. 715/215, 240
See application file for complete search history.

(56) References Cited

U.S. PATENT DOCUMENTS 5,279,294 A     1/1994  Anderson
5,689,742 A *   11/1997 Chamberlain, IV ... G03B 17/24
                                                    348/333.02
(Continued)

OTHER PUBLICATIONS

USPTO; Non-Final Office Action dated Mar. 7, 2016 in U.S. Appl. No. 14/219,985.
(Continued)

*Primary Examiner* — William Bashore
*Assistant Examiner* — Gregory A Distefano
(74) *Attorney, Agent, or Firm* — Snell & Wilmer L.L.P.

(57) ABSTRACT

Embodiments of the invention relate to a self-contained kit for medical condition monitoring and maintenance, such as the monitoring and maintenance of blood sugar levels. The kit is compact and includes components structurally retained therein for use without removal, wherein these components are normally separate and loose. Such components could include a glucose meter, an insulin pen and a lancing apparatus. Other embodiments of the invention relate to a computer system and method for monitoring a medical condition, monitoring a medical condition over time, correlating recorded results with environmental factors such as location, time and meals consumed. A method may also enable individual users to share information to provide support to one another.

19 Claims, 46 Drawing Sheets

Related U.S. Application Data filed on Mar. 15, 2013, provisional application No. 61/790,984, filed on Mar. 15, 2013, provisional application No. 61/791,141, filed on Mar. 15, 2013.

(51) Int. Cl.

| | | |
|---|---|---|
| *A61B 5/157* | (2006.01) | |
| *A61B 5/00* | (2006.01) | |
| *A61B 5/145* | (2006.01) | |
| *A61B 5/151* | (2006.01) | |
| *G01N 33/66* | (2006.01) | |
| *G06F 3/0481* | (2013.01) | |
| *G06F 3/0484* | (2013.01) | |
| *G06F 3/0488* | (2013.01) | |
| *A61M 5/315* | (2006.01) | |
| *A61B 5/0205* | (2006.01) | |
| *A61M 5/31* | (2006.01) | |

(52) U.S. Cl.
CPC ......... *G06F 3/04847* (2013.01); *G16H 10/60* (2018.01); *G16H 40/63* (2018.01); *A61B 5/0205* (2013.01); *A61M 2005/3126* (2013.01)

(56) References Cited

U.S. PATENT DOCUMENTS

| | | | |
|---|---|---|---|
| 5,728,074 A | 3/1998 | Castellano | |
| 8,058,077 B2 | 11/2011 | Groll | |
| 8,601,005 B2* | 12/2013 | Bousamra | G06F 19/3475 |
| | | | 600/365 |
| 2007/0016449 A1* | 1/2007 | Cohen | G06F 19/3406 |
| | | | 705/3 |
| 2008/0139910 A1 | 6/2008 | Mastrototaro et al. | |
| 2008/0201325 A1* | 8/2008 | Doniger | G06F 19/3468 |
| 2008/0294462 A1* | 11/2008 | Nuhaan | G06Q 10/06311 |
| | | | 705/3 |
| 2009/0113295 A1* | 4/2009 | Halpern | A61B 5/14532 |
| | | | 715/273 |
| 2009/0271729 A1* | 10/2009 | Killoren Clark | G06F 19/3406 |
| | | | 715/771 |
| 2010/0075353 A1* | 3/2010 | Heaton | A61B 5/0002 |
| | | | 435/14 |
| 2010/0077292 A1* | 3/2010 | Harris | H04N 1/2112 |
| | | | 715/232 |
| 2010/0274181 A1 | 10/2010 | Wang et al. | |
| 2010/0331651 A1* | 12/2010 | Groll | A61B 5/14532 |
| | | | 600/365 |
| 2011/0201911 A1* | 8/2011 | Johnson | A61B 5/14532 |
| | | | 600/365 |
| 2011/0275986 A1 | 11/2011 | Bashan et al. | |
| 2011/0282173 A1 | 11/2011 | Fonduca et al. | |
| 2012/0300089 A1* | 11/2012 | Sbaiz | H04N 1/00323 |
| | | | 348/222.1 |
| 2012/0303638 A1* | 11/2012 | Bousamra | G06F 19/3475 |
| | | | 707/751 |
| 2012/0046606 A1 | 12/2012 | Arefieg | |
| 2012/0330556 A1 | 12/2012 | Shaanan | |
| 2013/0172710 A1* | 7/2013 | Mears | G06F 19/3468 |
| | | | 600/365 |
| 2013/0197679 A1* | 8/2013 | Balakrishnan | G06F 17/40 |
| | | | 700/91 |
| 2013/0338464 A1 | 12/2013 | Stainken | |
| 2014/0337041 A1* | 11/2014 | Madden | G06F 19/322 |
| | | | 705/2 |
| 2015/0205930 A1* | 7/2015 | Shaanan | G06Q 10/00 |
| | | | 705/2 |
| 2015/0257692 A1 | 9/2015 | Refvik | |
| 2015/0260726 A1 | 9/2015 | Refvik | |
| 2015/0261928 A1 | 9/2015 | Refvik | |

OTHER PUBLICATIONS

USPTO; Non-Final Office Action dated Oct. 15, 2015 in U.S. Appl. No. 14/219,997.

PCT; International Search Report and Written Opinion dated Aug. 26, 2014 in Application No. PCT/US2014/030892.

USPTO; Final Office Action dated Nov. 25, 2016 in U.S. Appl. No. 14/219,985.

USPTO; Non-Final Office Action dated Jul. 5, 2016 in U.S. Appl. No. 14/219,997.

USPTO; Final Office Action dated Dec. 2, 2016 in U.S. Appl. No. 14/219,997.

USPTO; Final Office Action dated Dec. 19, 2016 in U.S. Appl. No. 14/219,991.

\* cited by examiner

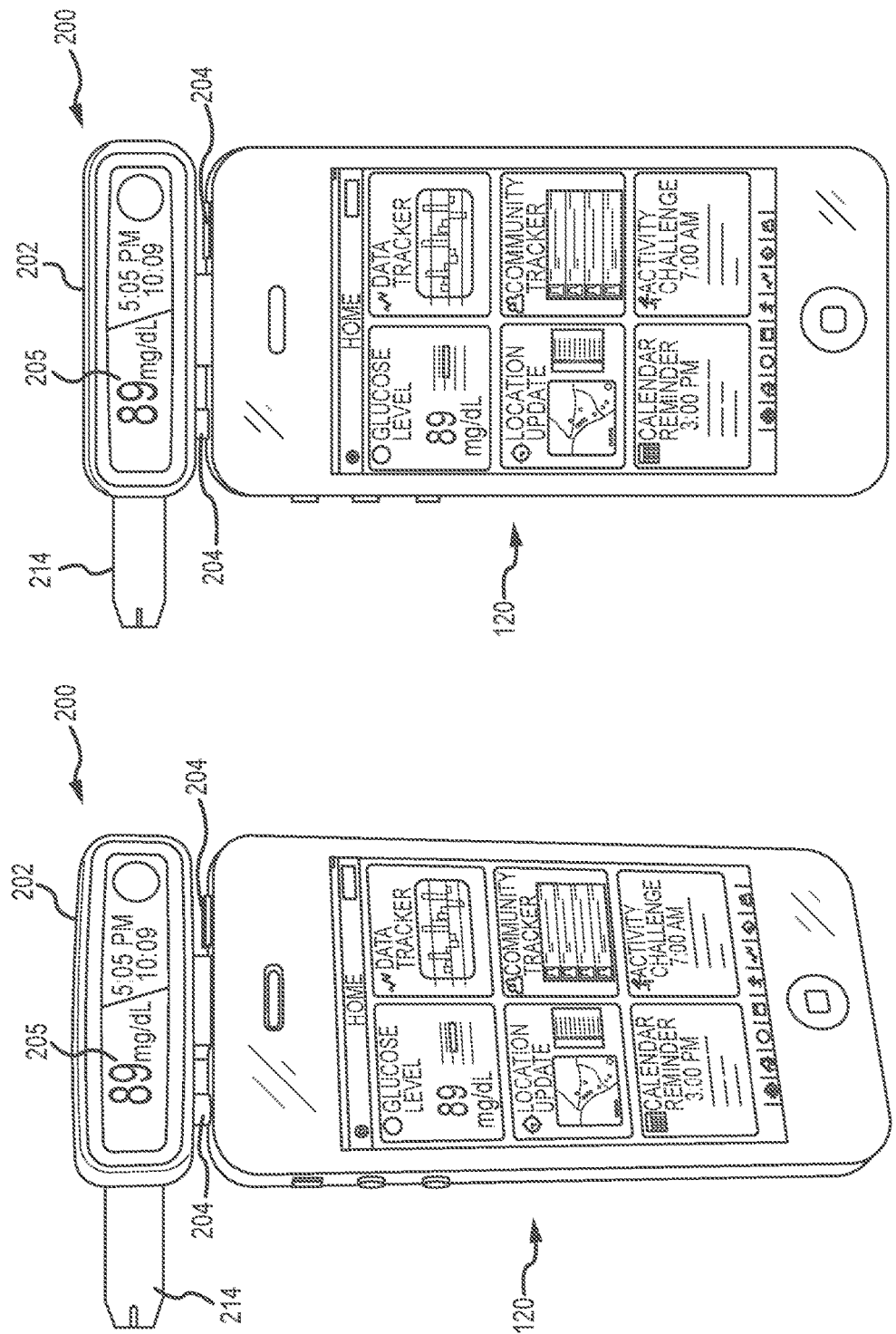

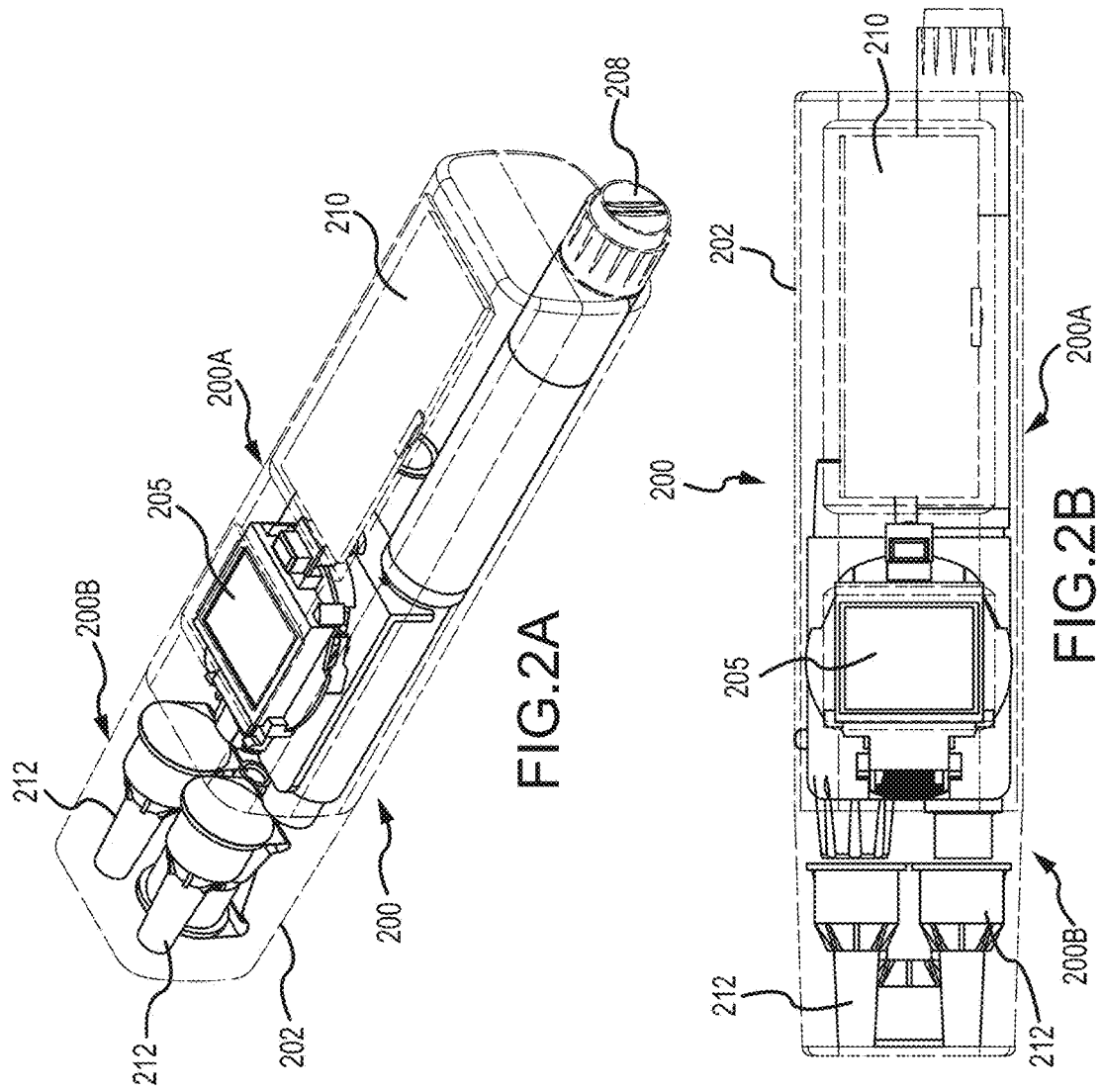

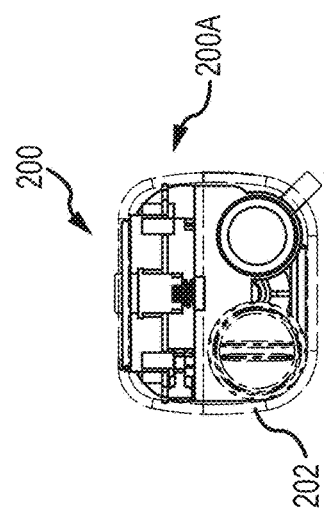
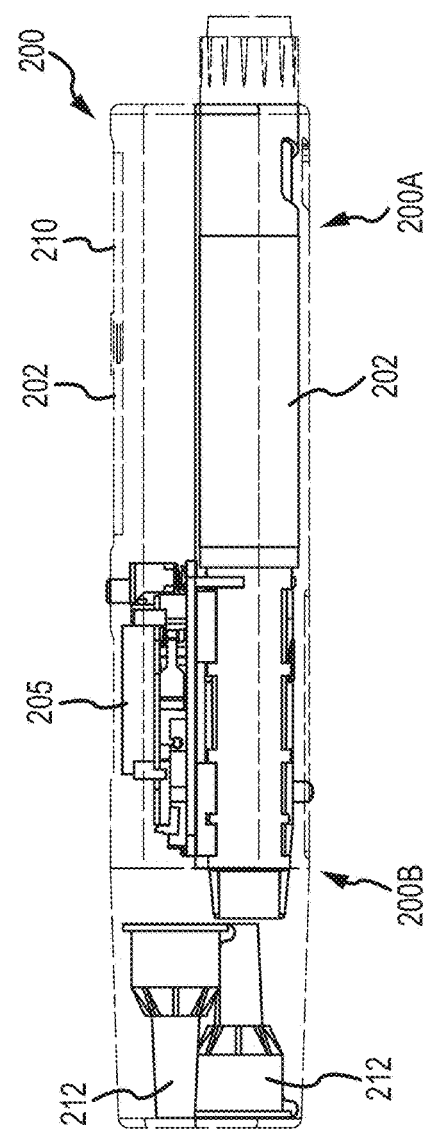
FIG.2D
FIG.2C

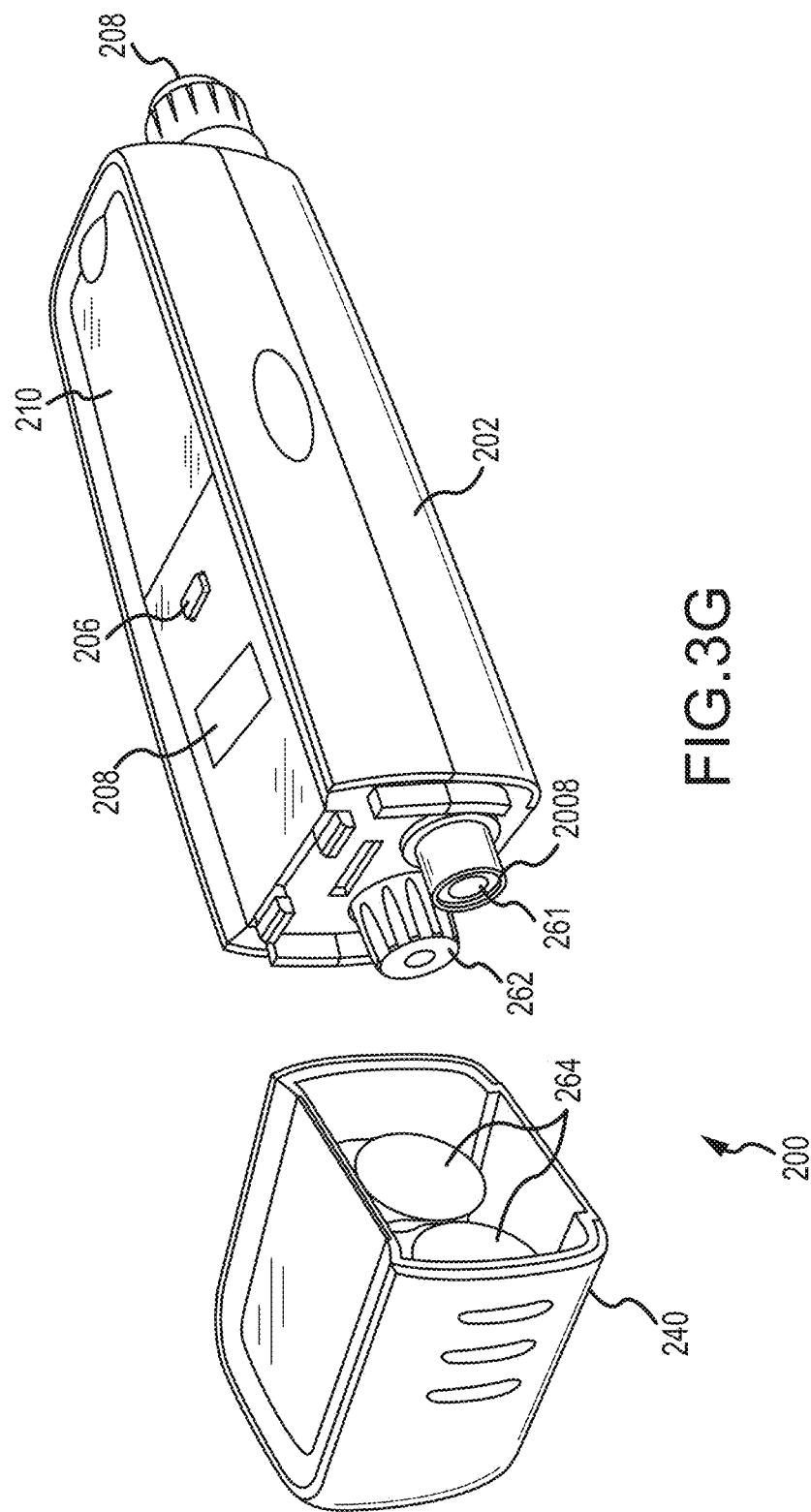

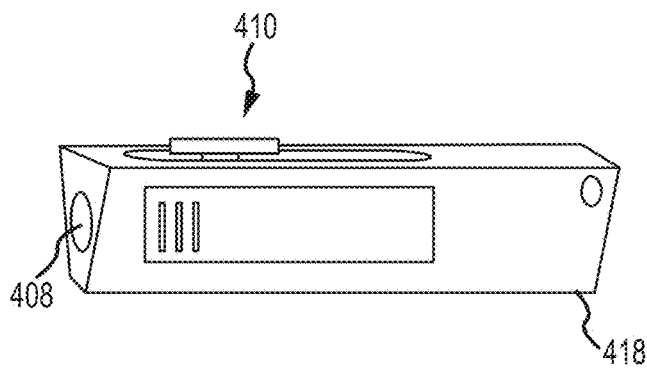
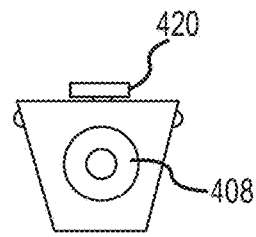
FIG.4A  FIG.4B
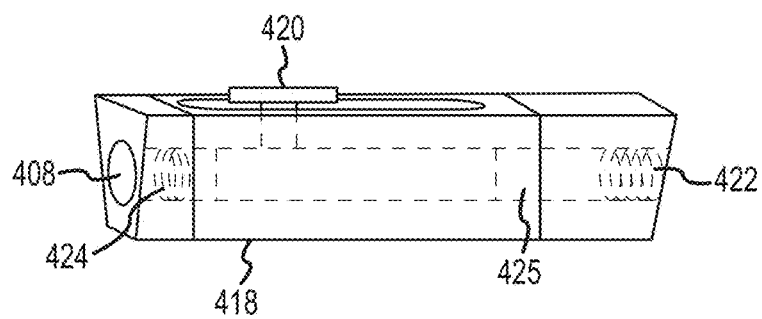
FIG.4C
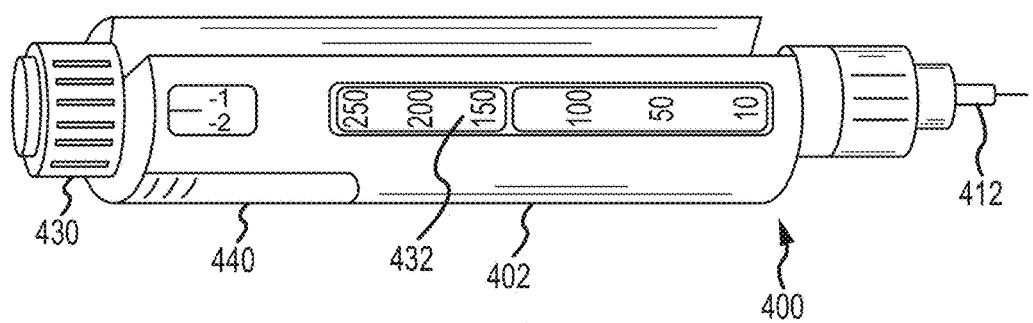
FIG.4D

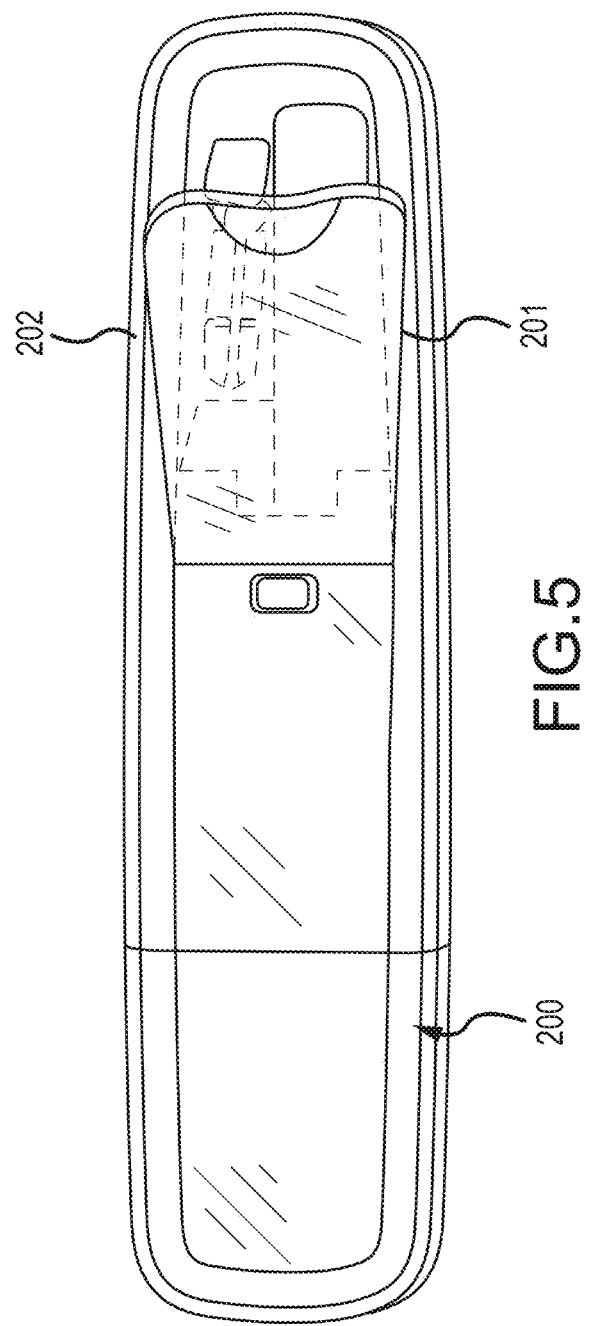

SYSTEMS AND METHODS FOR MANAGEMENT OF MEDICAL CONDITION

BACKGROUND

Particular medical conditions require periodic monitoring by the individual with the condition. With respect to diabetics, they must monitor their blood glucose level. Depending upon the type (Type I or Type II) of diabetes and severity, an individual may monitor his/her insulin level several times per day (particularly before and/or after meals), daily, weekly or monthly. To monitor one's glucose level a person typically lances a fingertip or thumb tip (collectively, "fingertip") to draw a drop of blood, place the blood on a test strip and insert the test strip into a device programmed to measure the glucose level (also referred to herein as "blood sugar" or "BS"). Depending upon the glucose level measured the person may inject him or herself with insulin, the amount of insulin being dependent upon the glucose measurement, or alternatively take an oral medication.

FIGS. 1J and 1K depict typical kits currently used by diabetics. FIG. 1J shows a kit with, among other things, lances, swabs, test strips and a glucose reader and FIG. 1K shows a kit that includes insulin pens (each of which contains insulin and can be adjusted to dispense a predetermined amount of insulin) and needles. Each kit is approximately 4"×5"×1½" and many diabetics must carry both kits when traveling, or even when going to a restaurant. Hence, there is a need for a smaller, more compact manner for a diabetic to carry necessary testing and treatment supplies. There is also a need for a fast and simple way to effectuate the measurement of one's blood glucose level and for administering insulin (if required).

Diabetics can also benefit from a system and method that provides an historical record of blood sugar level and can correspond the history of blood glucose measurement to different meals and/or dining at particular restaurants. With this information a diabetic can select different restaurants and/or meals in the future. Further, a diabetic can quickly review, for example, in a graphical format his or her glucose level over a period of hours, days, a week, a month or any given period, to see and evaluate a history of how well he or she is controlling glucose levels.

SUMMARY

Embodiments of the present invention are directed to systems and methods for the management of a medical condition, and more particularly to the management of a medical condition that requires periodic monitoring. References herein are made to specific examples wherein the medical condition is diabetes. However, the concepts described herein are applicable to other medical conditions, including, but not limited to managing, cholesterol level, blood pressure, heart rate or function, sodium levels, potassium levels, creatinine levels, liver function, or other medical conditions.

Thus, the most preferred embodiments of the present disclosure variously address the monitoring and testing of blood glucose levels, the administration of insulin (if required), and a system and method for a diabetic to quickly see his/her glucose history, compare the history with restaurants and/or meals, and, if desired, to share information with others to form a support group.

A kit (also referred to herein sometimes as a "device") according to aspects of the invention is self-contained and approximately 5"-6" in length, 1"-1½" wide and 1"-1½" deep. The kit may include a first compartment that includes lances to lance a fingertip and test strips upon which blood is placed. The kit may have a second compartment that includes needles. The kit also includes a lancing apparatus, an insulin pen that preferably can be manually adjusted to administer a desired amount of insulin and a needle mount that communicates with the insulin pen. The kit also includes a glucose meter that determines the blood glucose level from the blood placed on a test strip.

A kit according to aspects of the invention replaces the two prior art kits described above, is small enough to fit in a pocket or a purse, and at some major components, such as the insulin pen, glucose meter and lancing apparatus, are self-contained within the kit and are not removed during use. During use a test strip is removed from a compartment of the kit and is positioned in a slot (or part) in the kit housing. The slot communicates with an opening in the glucose meter and when the test strip is inserted the glucose meter is activated. The person then exposes an end of the lancing apparatus (if not already exposed), which is preferably an opening in the kit housing, inside of which is a spring-loaded lance. The user presses a fingertip to the opening and presses a button on the kit housing. The button releases the lance for a predetermined distance so the lance slightly pricks the fingertip to draw blood.

When the fingertip is lanced the user places a drop of blood on the test strip and the glucose meter measures and provides the blood glucose level, preferably by a digital, electronic display. To conserve power, the glucose meter is preferably only activated when a test strip is inserted.

Depending on the blood glucose level, the user may wish to inject him or herself with insulin. The user would first adjust (or select) the amount of insulin to be injected by an adjustment device connected to the insulin pen. Then a needle is removed from the second compartment. In the embodiments shown, the insulin pen has an end opposite the adjustment device and this end receives a needle. Once the needle is received (or mounted) to the end of the insulin pen the user can inject insulin in a standard manner. Afterwards, the needle is removed and discarded and the kit is put away.

In another embodiment in the kit includes either a wired or wireless communication device to communicate with a mobile device (such as a smart phone) or a computer. Alternatively, the kit itself may have a processor and data storage to retain data. In either mode, the user's glucose readings can be automatically stored and/or transmitted. The information transmitted from the kit can include the glucose reading, time and date the reading was made, the amount of insulin injected, the glucose reading after the insulin injection, and environmental information, such as the location where the reading was taken, whether it was before or after a meal, the type of meal consumed, and the name of restaurant or other establishment where the meal was consumed. This information can be stored and utilized by a software program (either in the kit, a smart phone, computer, or one that is accessed via the internet by any such device): (a) to create a chart or graphical display of glucose readings over a given time period, and/or (b) correlate readings with different meals at different places to create a history for the user.

This data allows user to interactively track history and enter information about each blood sugar test/result. If the data is stored in a central location, such as a website, the user/medical professionals can access the information and track progress and adjust the user's treatment plan as necessary. A system or method according to the invention may also alert user/medical professional of problems or irregularities, and can be updated with additional test results such as blood results/A1C results to better gain the overall health of the user. The application may also learn the habits of the user such as meals/testing times and send out reminders to users. All or some of the data may also be shared with other persons to create a support group, as further described below.

Both the foregoing summary and the following detailed description are exemplary and explanatory only and are not restrictive of the present disclosure or claims.

BRIEF DESCRIPTION OF THE DRAWINGS

A more complete understanding of the embodiments of the present disclosure may be derived by referring to the detailed description and claims when considered in connection with the following illustrative figures.

FIGS. 1F-1I illustrate the embodiment of FIG. 1A connected to an exemplary mobile device.

FIG. 2A illustrates a side, perspective, phantom view of a second embodiment in accordance with the present invention.

FIG. 2B illustrates a top phantom view of the embodiment of FIG. 2A.

FIG. 2C illustrates a side phantom view of the embodiment of FIG. 2A.

FIG. 2D illustrates an end phantom view of the embodiment of FIG. 2A with cap 200B removed.

FIGS. 3A-3G illustrate other views of the embodiment in accordance with the FIGS. 2A-2F.

FIG. 4A is a side view of a lancet apparatus that may be used in accordance with aspects of the invention.

FIG. 4B is an end view of the lancet apparatus of FIG. 4A.

FIG. 4C is a side, partial view of the lancet apparatus of FIG. 4A.

FIG. 4D is a side view of an insulin pen that may be used in accordance with aspects of the invention.

FIG. 5 is a top view of the embodiment of FIG. 2A with a cavity partially open.

FIGS. 21-34 illustrate screenshots of a display for use in connection with an exemplary system for managing a medical condition.

DETAILED DESCRIPTION

Figure 1A:
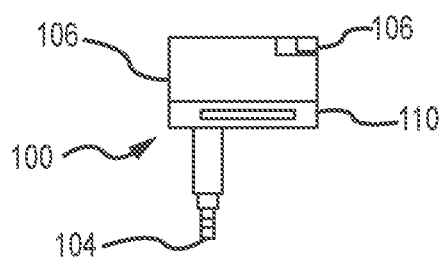
FIG. 1A illustrates a front view of a first embodiment of a device in accordance with the present invention that can be attached to a mobile device, such as a smart phone.
Figure 1B:
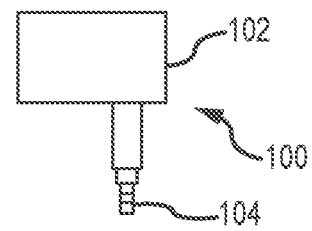
FIG. 1B illustrates a rear view of the embodiment of FIG. 1A.
Figure 1C:
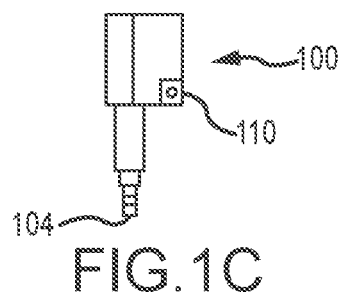
FIG. 1C illustrates a left side, perspective view of the embodiment of FIG. 1A.
Figure 1D:
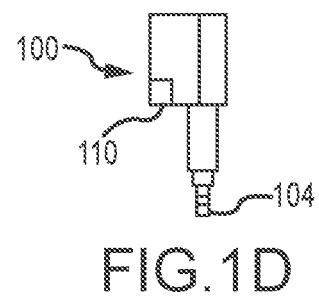
FIG. 1D illustrates a right side, perspective view of the embodiment of FIG. 1A.
Figure 1E:
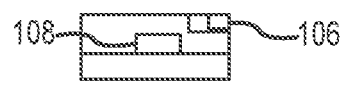
FIG. 1E illustrates a top view of the embodiment of FIG. 1A.
Figure 1F:
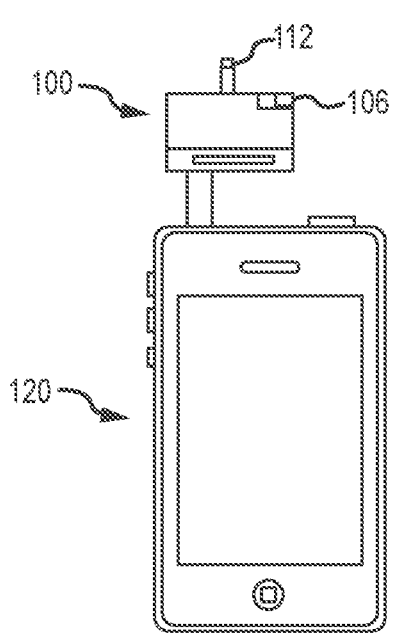
Figure 1G:
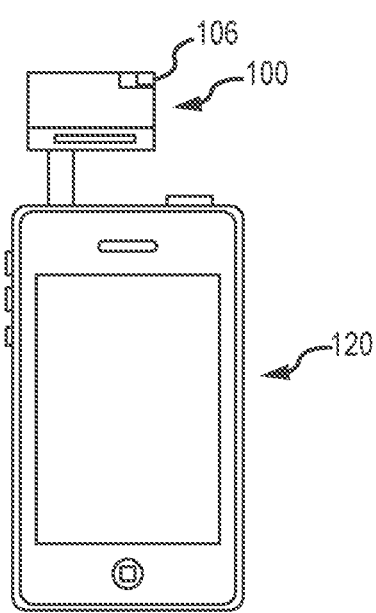
Figure 1K:
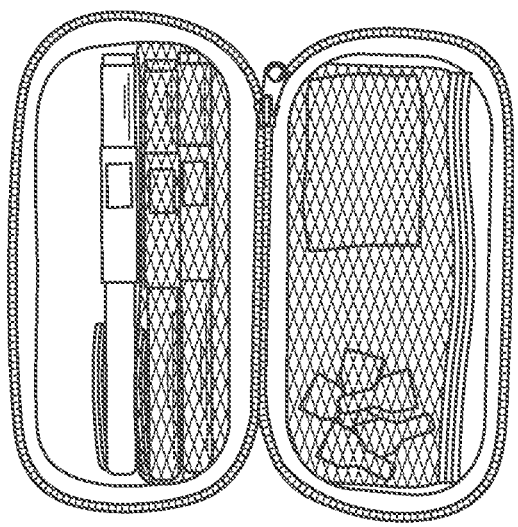
FIG. 1K shows another prior art kit that houses loose components that are removed and used separately.
Figure 1J:
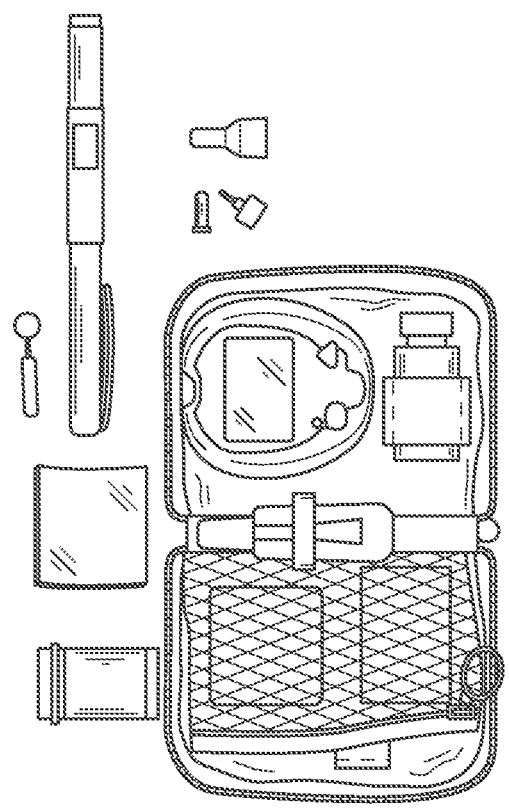
FIG. 1J shows a prior art kit that houses loose components that are removed and used separately.
Figure 2E:
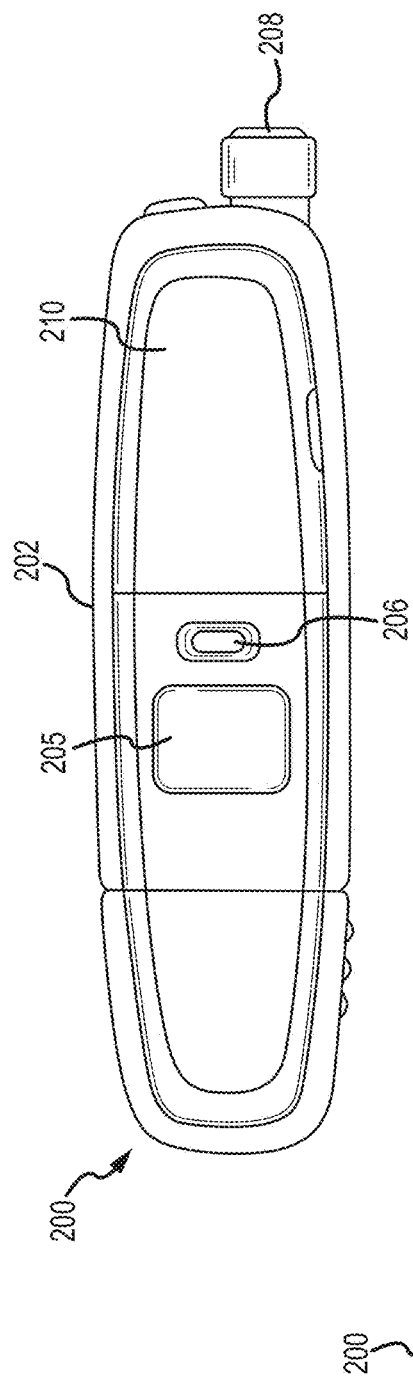
FIG. 2E is a top view of the embodiment of FIG. 2A.
Figure 2F:
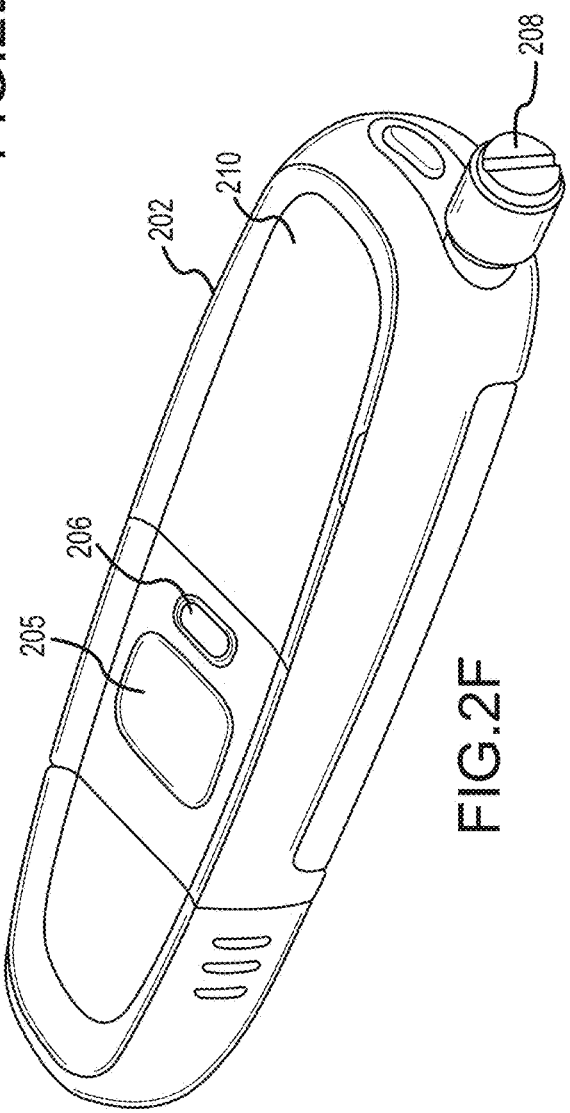
FIG. 2F is a perspective side view of the embodiment of FIG. 2A.

The detailed description of exemplary embodiments herein makes reference to the accompanying figures, which show the exemplary embodiments by way of illustration. While these exemplary embodiments are described in sufficient detail to enable those skilled in the art to practice the inventions herein, it should be understood that other embodiments may be realized and that logical and mechanical changes may be made without departing from the spirit and scope of the disclosure.

Referring now to FIGS. 1A-1I, which are collectively referred to as FIG. 1, a first embodiment of a diabetes management kit assembly 100 comprises: a body assembly 102, an auxiliary jack 104 for connection to a smart phone or other computer device, LED indicator lights 106, an opening 108 for a lancet, and a storage door for storing lancets 110. A plurality of lancets 110 and test strips can be stored in the storage area of body assembly 102 that is accessed by the storage door. In an exemplary embodiment, a daily usage of lancets (e.g., three lancets) and test strips (e.g., 10 test strips) can be stored in the storage area.

Diabetes management kit assembly 100 may communicate with a computer (or computing) device 120 through a wired connection (auxiliary jack 104), such as a universal serial bus (USB) connection, a computer network connection, a mobile device synchronization port connection, a power connection, and/or a security cable. Alternatively, diabetes management kit assembly 100 may communicate with computer device 120 through any desired wireless connection, such as a wireless Internet connection, a Bluetooth connection, a cellular telephone network connection, a CDMA/GSM/4G LTE network, a wireless LAN connection, a wireless WAN connection, and/or an optical connection.

In accordance with exemplary embodiments, computer device 120 comprises any type of computing device, such as a smart phone, a tablet computer, a laptop computer, a desktop computer, a mobile subscriber communication device, a mobile phone, and/or a personal digital assistant (PDA).

In operation, a small drop of blood is obtained from the user, by pricking the skin with lancet 110 that protrudes through an opening. The drop of blood is placed on the disposable test strip. The diabetes management kit assembly 100 reads the test strip to calculate the blood glucose level of the user. LED indicator lights 106 are used to display the level of the blood glucose level. For example, a red light indicates a poor or out of normal range reading, while a green light indicates a good or in normal range reading.

Referring now to FIGS. 2A-F, which are collectively referred to as FIGS. 2, 3A-G, which are collectively referred to herein as FIG. 3, FIGS. 4A-F, which are collectively referred to as FIG. 4, and FIGS. 5-18, another embodiment of a diabetes management kit assembly 200 comprises: a body assembly 202, a digital readout window 205, LED indicator light/on-off button 206, a pre-loaded insulin pen 208, a storage door 210 for storing lancets, lancets and needles 212, and test strips 214. A plurality of needles 212 and test strips 214 can be stored in the storage area of body assembly 202 that is accessed by storage door 210.

Diabetes management kit assembly 200 may communicate with computer device 120 through a wired connection (auxiliary jack 204), as described above. Alternatively, diabetes management kit assembly 200 may communicate with computer device 120 through any desired wireless connection, such as a wireless Internet connection, a Bluetooth connection, a cellular telephone network connection, a CDMA/GSM/4G LTE network, a wireless LAN connection, a wireless WAN connection, and/or an optical connection.

In operation, a small drop of blood is obtained from the user, by pricking the skin with the lancet that protrudes through an opening. The drop of blood is placed on the disposable test strip. The diabetes management kit assembly 200 reads the test strip to calculate the blood glucose level of the user. Digital readout window 205 displays the blood glucose level of the user. LED indicator lights 206 are used to indicate the level of the blood glucose level. For example, a red light indicates a poor or out of normal range reading, while a green light indicates a good or in normal range reading.

LED indicator lights/on-off button 206 also operates as an on/off button for the test kit. The user can press button 206 to turn the kit on or off, and to see the last several blood glucose results.

Referring now to FIGS. 3A-G, which are collectively referred to as FIG. 3, diabetes management kit assembly 200 comprises: a body assembly 202, a digital readout window 205, LED indicator light/on-off button 206, a pre-loaded insulin pen 208, and a storage door 210 for storing lancets and test strips. A plurality of lancets and test strips can be stored in the storage area of body assembly 202 that is accessed by storage door 210.

Figure 3B:
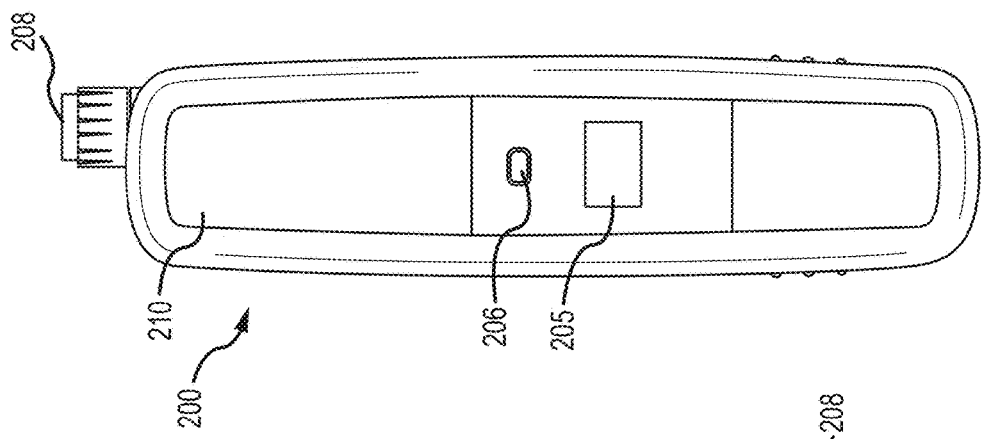
Figure 3A:
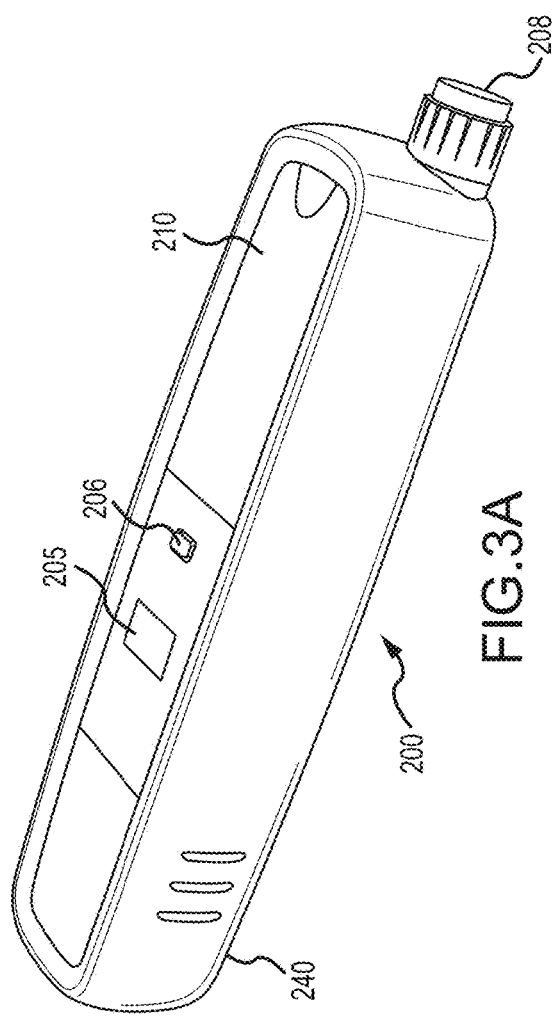
Figure 3C:
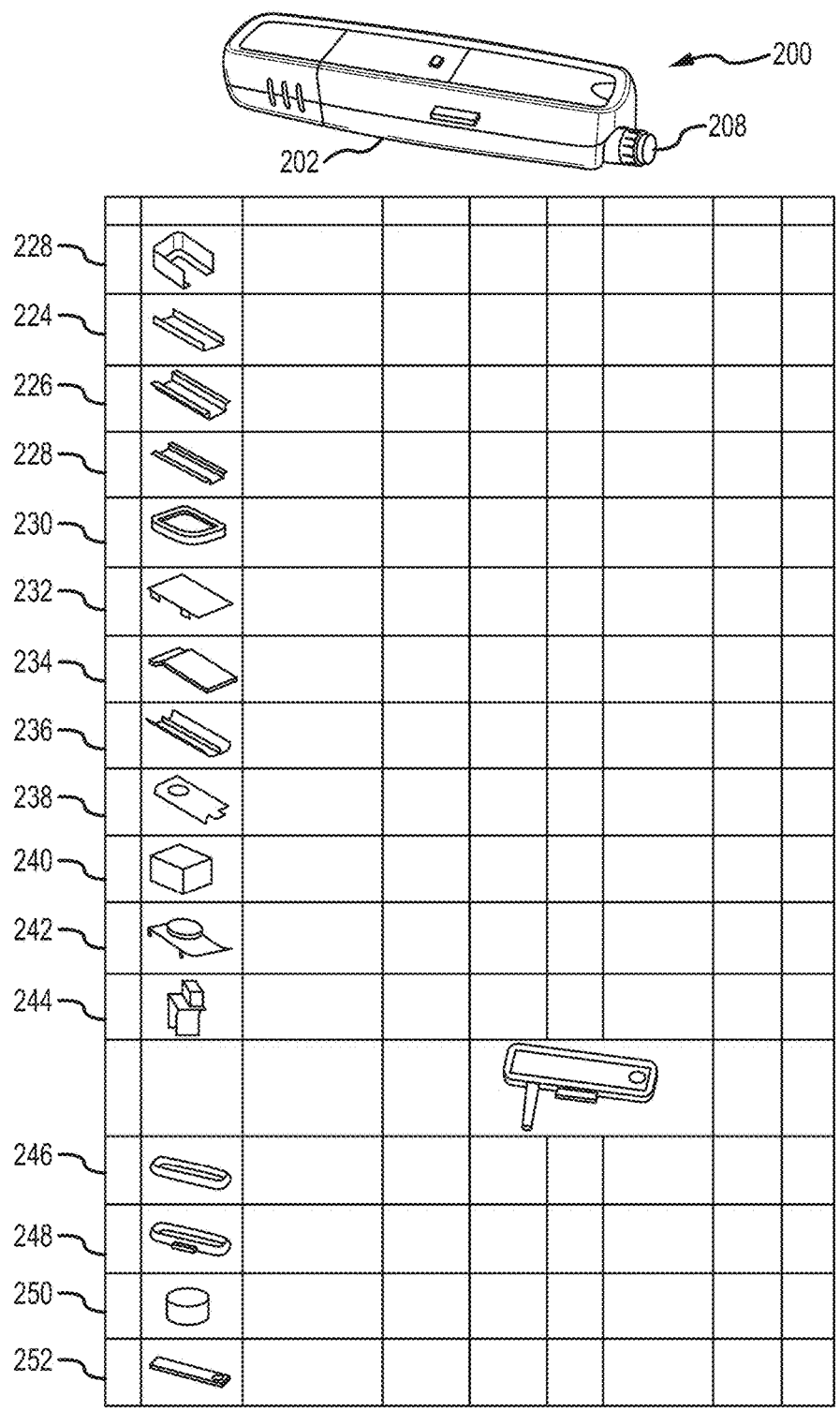
Figure 3D:
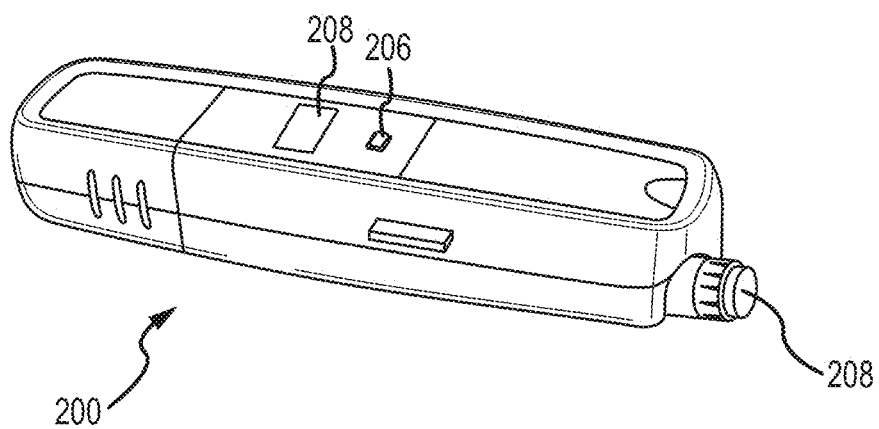

With reference to FIG. 3C, diabetes management kit assembly 200 comprises a plurality of molded components, including: a cap frame 228, a top frame 224, a base frame 226, a first window 228, a second window 230, a lens 232, a lid 234, a base 236, a top 238, a cap 240, a battery plate 242, a battery button 244, an overmold module 246, a housing module 248, a button module 250, and a lens module 252.

In this embodiment, cap frame 228 may be made from 60 A durometer urethane material from a cast elastomer process, with a matte finish. Alternatively, cap frame 228 can be made from other materials as requirements allow.

In this embodiment, top frame 224 may be made from 60 A durometer urethane material from a cast elastomer process, with a matte finish. Alternatively, top frame 224 can be made from other materials as requirements allow.

In this embodiment, base frame 226 may be made from 60 A durometer urethane material from a cast elastomer process, with a matte finish. Alternatively, base frame 226 can be made from other materials as requirements allow.

First window 228 and second window 230 may be machined from polished acrylic, with a glossy finish. First window 228 and second window 230 have a clear color so that the user can see through the windows. Alternatively, first window 228 and second window 230 can be made from other suitable material such as glass, plexiglass, or other appropriate material.

Lens 232 may be machined from polished acrylic, with a glossy finish. Lens 232 has a clear color so that the user can see through the lens. Alternatively, lens 232 can be made from other suitable material such as glass, or other appropriate material.

Lid 234 may be machined from thermoplastic, such as acrylonitrile butadiene styrene, with a glossy finish. Alternatively, lid 234 can be made from other suitable thermoplastic, or other appropriate material.

Base 236 may be machined from thermoplastic, such as acrylonitrile butadiene styrene, with a glossy finish. Alternatively, base 236 can be made from other suitable thermoplastic, or other appropriate material.

Top 238 may be machined from thermoplastic, such as acrylonitrile butadiene styrene, with a glossy finish. Alternatively, top 338 can be made from other suitable thermoplastic, or other appropriate material.

Cap 240 may be machined from thermoplastic, such as acrylonitrile butadiene styrene, with a glossy finish. Alternatively, cap 240 can be made from other suitable thermoplastic, or other appropriate material.

Battery plate 242 may be machined from thermoplastic, such as acrylonitrile butadiene styrene, with any finish. Alternatively, battery plate 242 can be made from other suitable thermoplastic, or other appropriate material.

Battery button 244 may be machined from thermoplastic, such as acrylonitrile butadiene styrene, with a glossy finish. Alternatively, battery button 344 can be made from other suitable thermoplastic, or other appropriate material.

Overmold module 246 may be made from 60 A durometer urethane material from a cast elastomer process, with a matte finish. Alternatively, overmold module 346 can be made from other materials as requirements allow.

Housing module 248 may be machined from thermoplastic, such as acrylonitrile butadiene styrene, with a glossy finish. Alternatively, housing module 248 can be made from other suitable thermoplastic, or other appropriate material.

Button module 250 may be machined from thermoplastic, such as acrylonitrile butadiene styrene, with a glossy finish. Alternatively, button module 250 can be made from other suitable thermoplastic, or other appropriate material.

Lens module 252 may be made from acrylic, with a glossy finish. Alternatively, lens module 252 can be made from other suitable material such as glass, or other appropriate material.

Figure 3E:
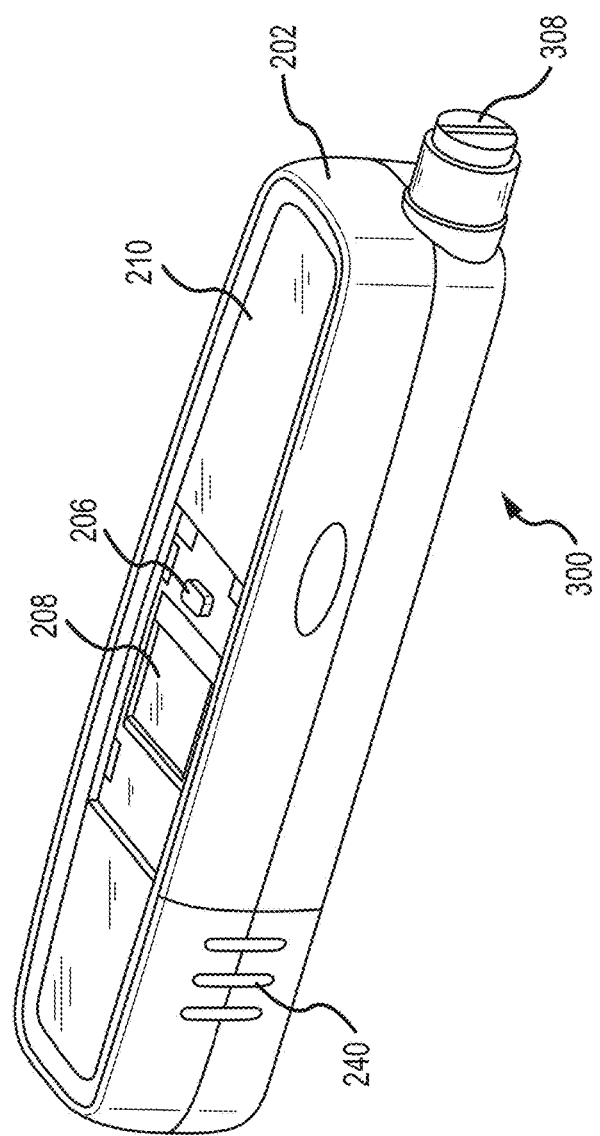
Figure 3F:
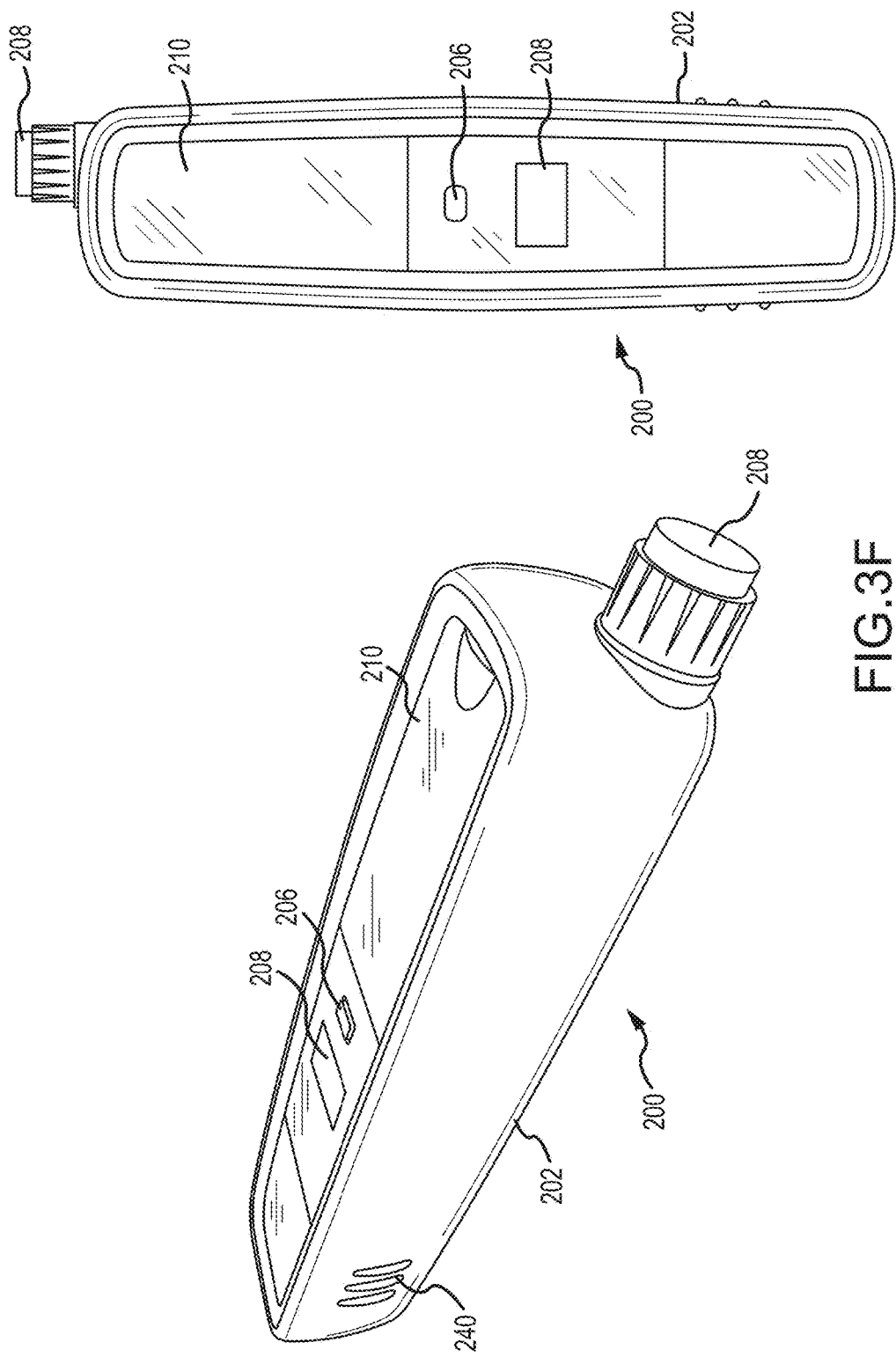

With reference to FIGS. 3E and 3G, diabetes management kit assembly 200 further comprises cap 340 that is removable from body assembly 202. Insulin pen 208 and lancet device 262 are positioned in body assembly 202 through the use of an expandable insert to allow different types of insulin pens to fit into the kit. In addition, needles are stored in cartridges 264, which are stored in cap 240. In accordance with this embodiment, a loaded lancet device 262 can hold a plurality of lancets. For example, a loaded lancet device may hold 7-10 lancets for use over a 2-3 day period, or more. Once loaded, one needle (lancet) will extend automatically from lancet device 262 through the opening. When a lancet is used, it will retract into lancet device 262 for later disposal.

In addition, a loaded cartridge is provided that will hold a plurality of test strips, for example 8-10, for one or more days of testing. The test strip cartridge will be loaded into a feeder, so that when engaged, it will automatically load one test strip into the glucose meter for testing. Once used, the test strip will either be ejected for disposal, or the test strip will be stored in the cartridge for later disposal. In addition, diabetes management kit assembly 200 will include an alcohol dispensing apparatus for automatically dispensing alcohol swabs for the user to clean the skin and the kit for insulin injections.

Diabetes management kit assembly 200 may communicate with a device, such as computer device 120, through a wired connection, as described above. Alternatively, diabetes management kit assembly 200 may communicate with computer device 120 through any desired wireless connection, such as a wireless Internet connection, a Bluetooth connection, a cellular telephone network connection, a CDMA/GSM/4G LTE network, a wireless LAN connection, a wireless WAN connection, and/or an optical connection.

In operation, a small drop of blood is obtained from the user, by pricking the skin with a lancet that protrudes from lancet device 260. The drop of blood is placed on the disposable test strip. The diabetes management kit assembly 200 reads the test strip to calculate the blood glucose level of the user. Digital readout window 205 displays the blood glucose level of the user. LED indicator lights 206 are used to indicate the level of the blood glucose level. For example, a red light indicates a poor or out of normal range reading, while a green light indicates a good or in normal range reading.

Figure 4E:
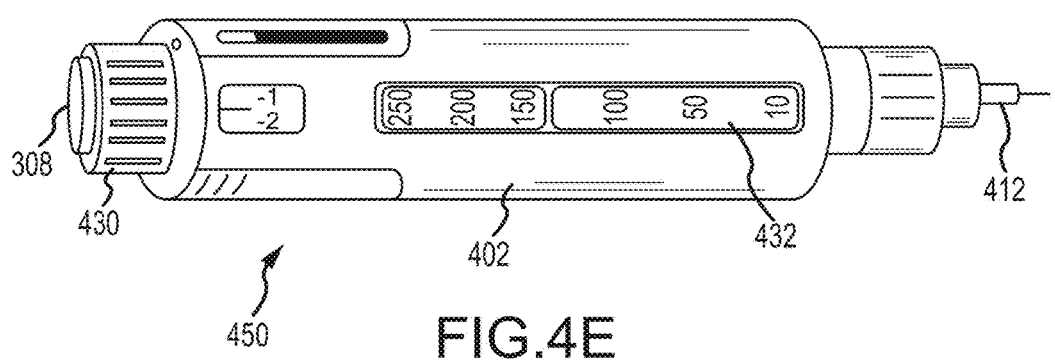
FIG. 4E is another side view of an insulin pen that may be used in accordance with aspects of the invention.
Figure 4F:
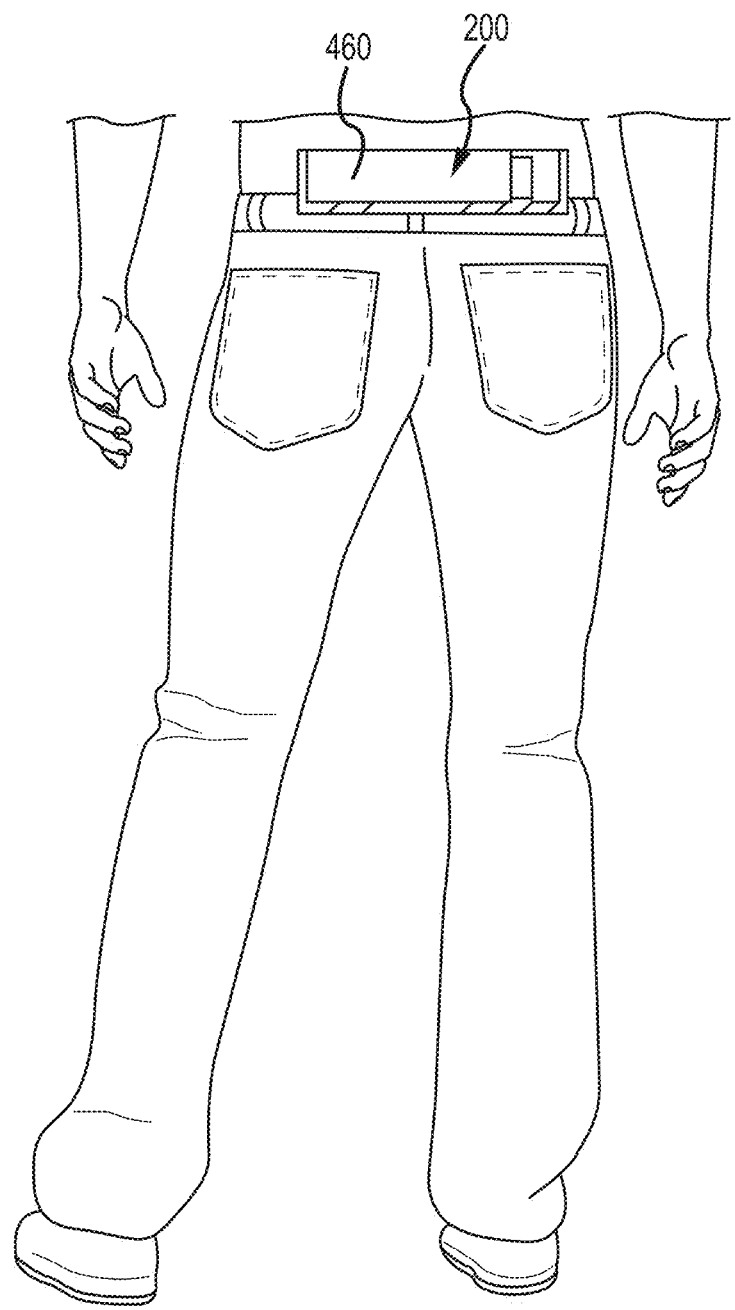
FIG. 4F shows a device according to aspects of the invention worn on a belt.

Referring now to FIGS. 4A-4F, which are collectively referred to as FIG. 4, embodiments of a lancet assembly and insulin pen are shown. Lancet assembly 400 comprises an internal frame 418, a lancet trigger 420, and internal springs 422 and 424.

Internal frame 418 includes a shaft 425, wherein internal springs 422 and 424 are positioned in shaft 425. Shaft 425 is situated to hold and direct the lancet in one direction. Internal spring 424 is located near lancet exit hole 408, such that internal spring 424 is positioned to stop the lancet, and along with internal frame 418 keep the lancet from exiting too far from assembly 400. Internal spring 424 is positioned to stop the lancet and return the needle inside of carrying case, one shot at a time. Internal spring 422 is located in the far end of shaft 425 from internal spring 424. Internal spring 422 projects the lancet towards exit hole 408 to puncture the finger of the user. Lancet trigger 420 is used to initiate the projection of the lancet.

Insulin pen 450 comprises an insulin adjustment knob 430 (on its first end) and insulin level display window 432. In operation, insulin adjustment knob 430 is used to adjust the amount of insulin to administer to the user. The amount of insulin that will be administered is displayed in insulin level display window 432. Insulin pen 450 also includes a second end for mounting a needle 412.

Figure 6:
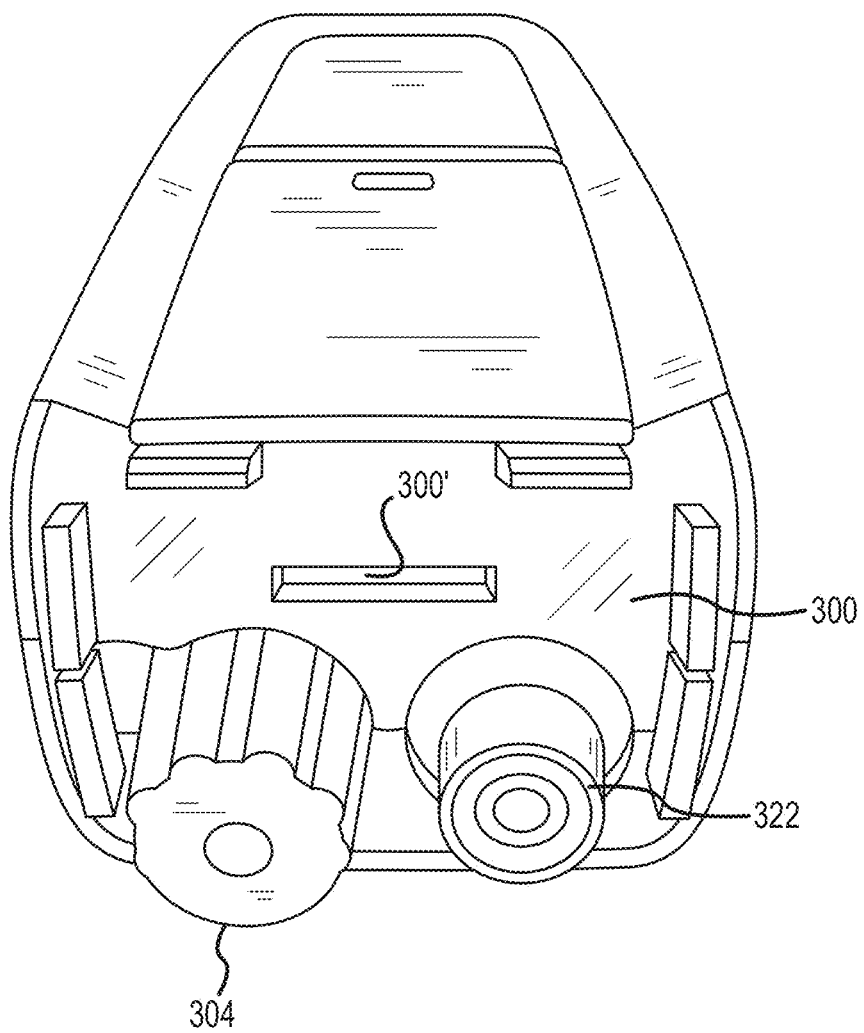
FIG. 6 is a perspective end view of the embodiment of FIG. 2A with cap 200B removed.
Figure 7:
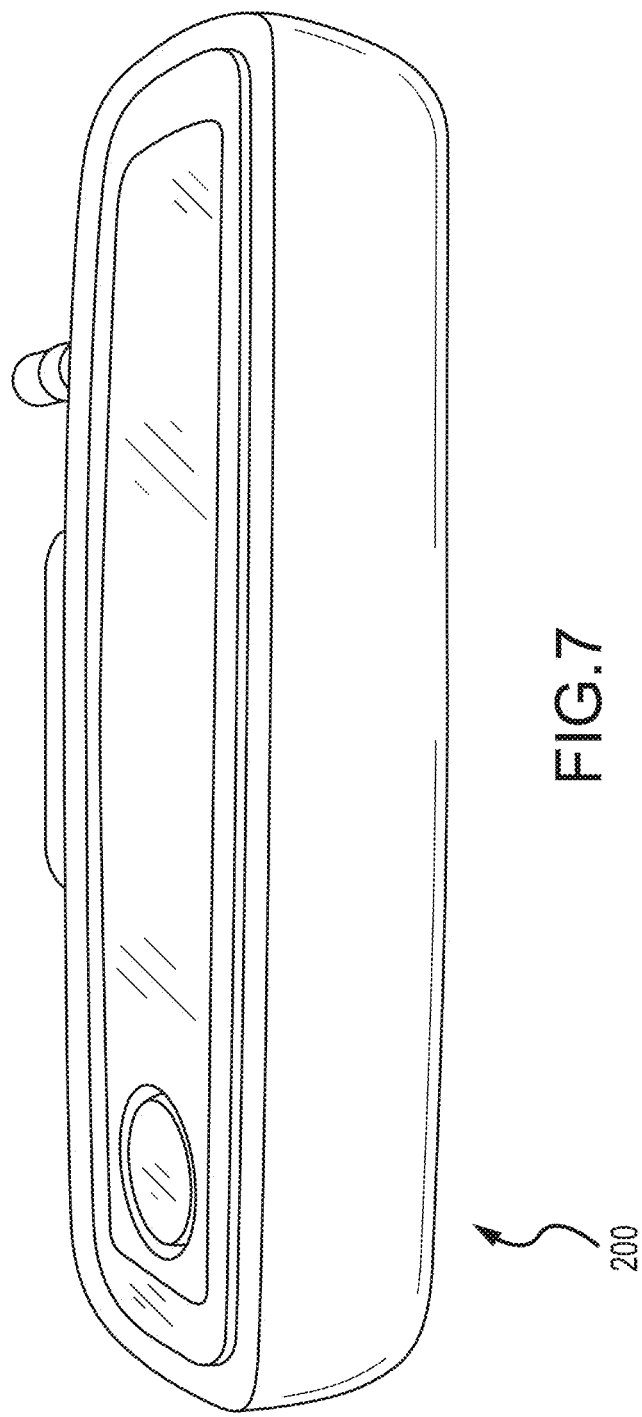
FIG. 7 is a perspective side view of the embodiment of FIG. 2A showing the bottom surface.
Figure 8:
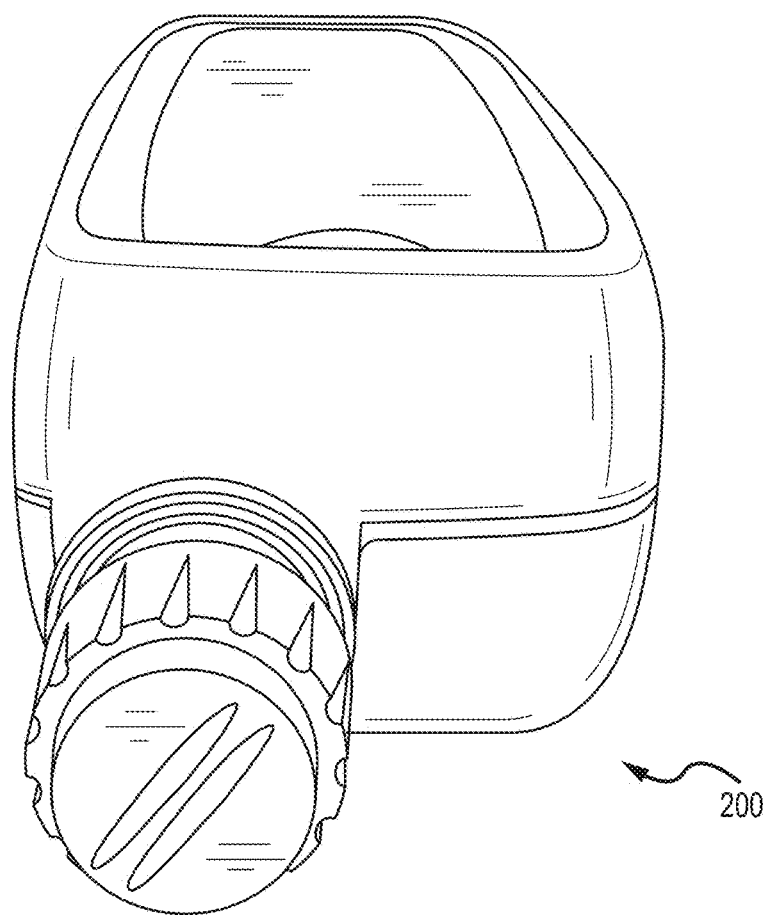
FIG. 8 is a perspective end view of the embodiment of FIG. 2A showing the insulin pen adjustment mechanism.
Figure 9:
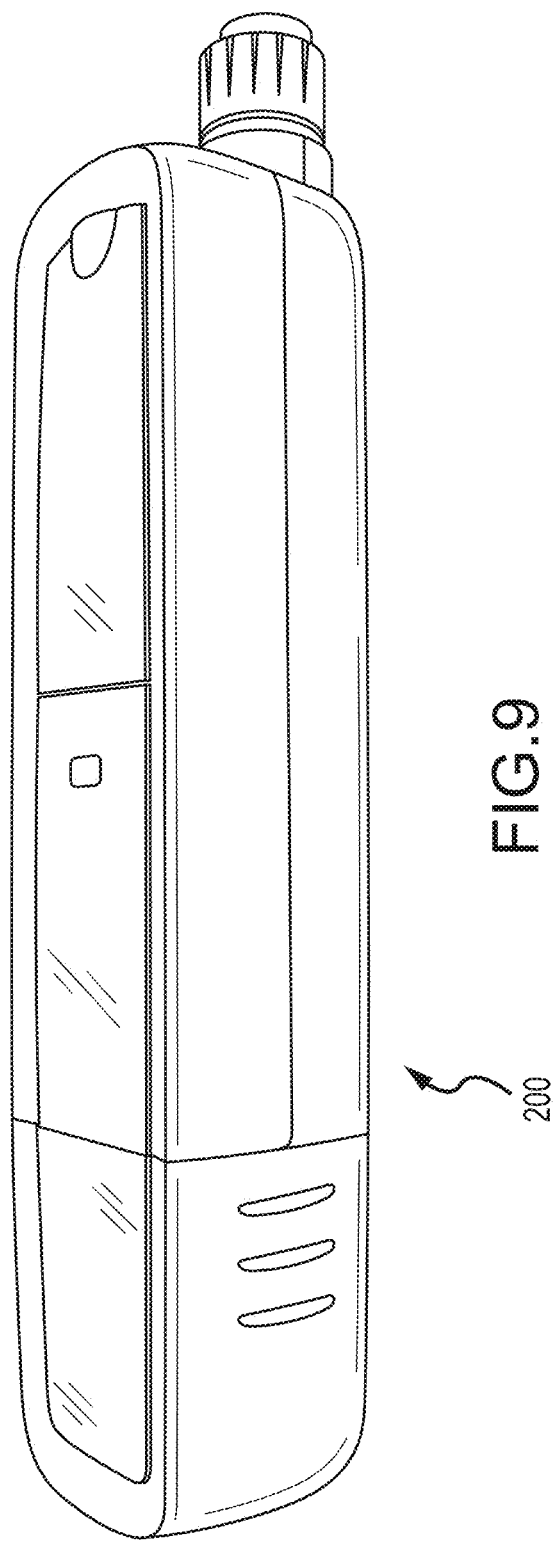
FIG. 9 is a perspective side view of the embodiment of FIG. 2A showing the top surface.
Figure 10:
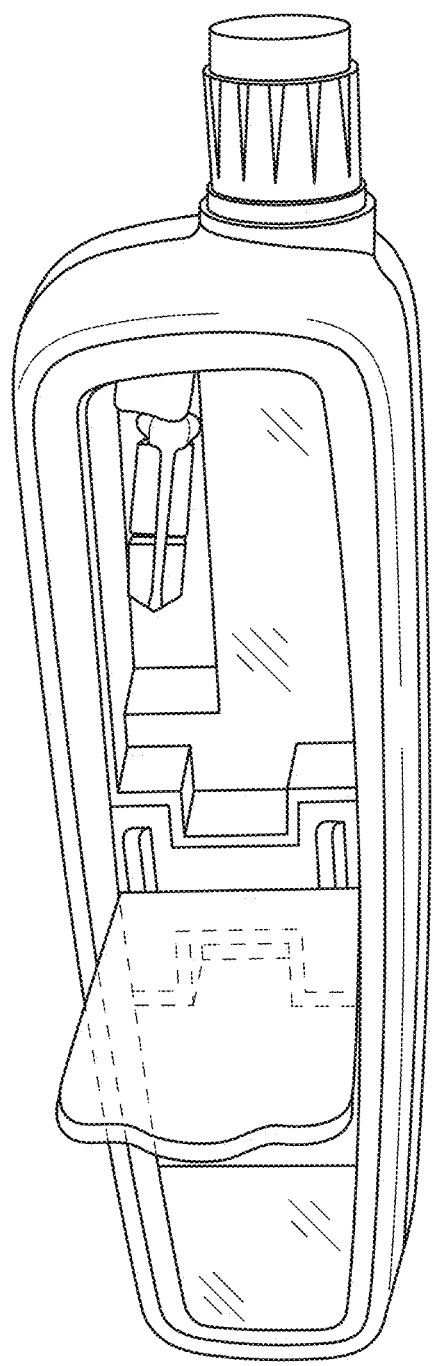
FIG. 10 is a perspective top view of the embodiment of FIG. 2A showing the compartment fully open.
Figure 11:
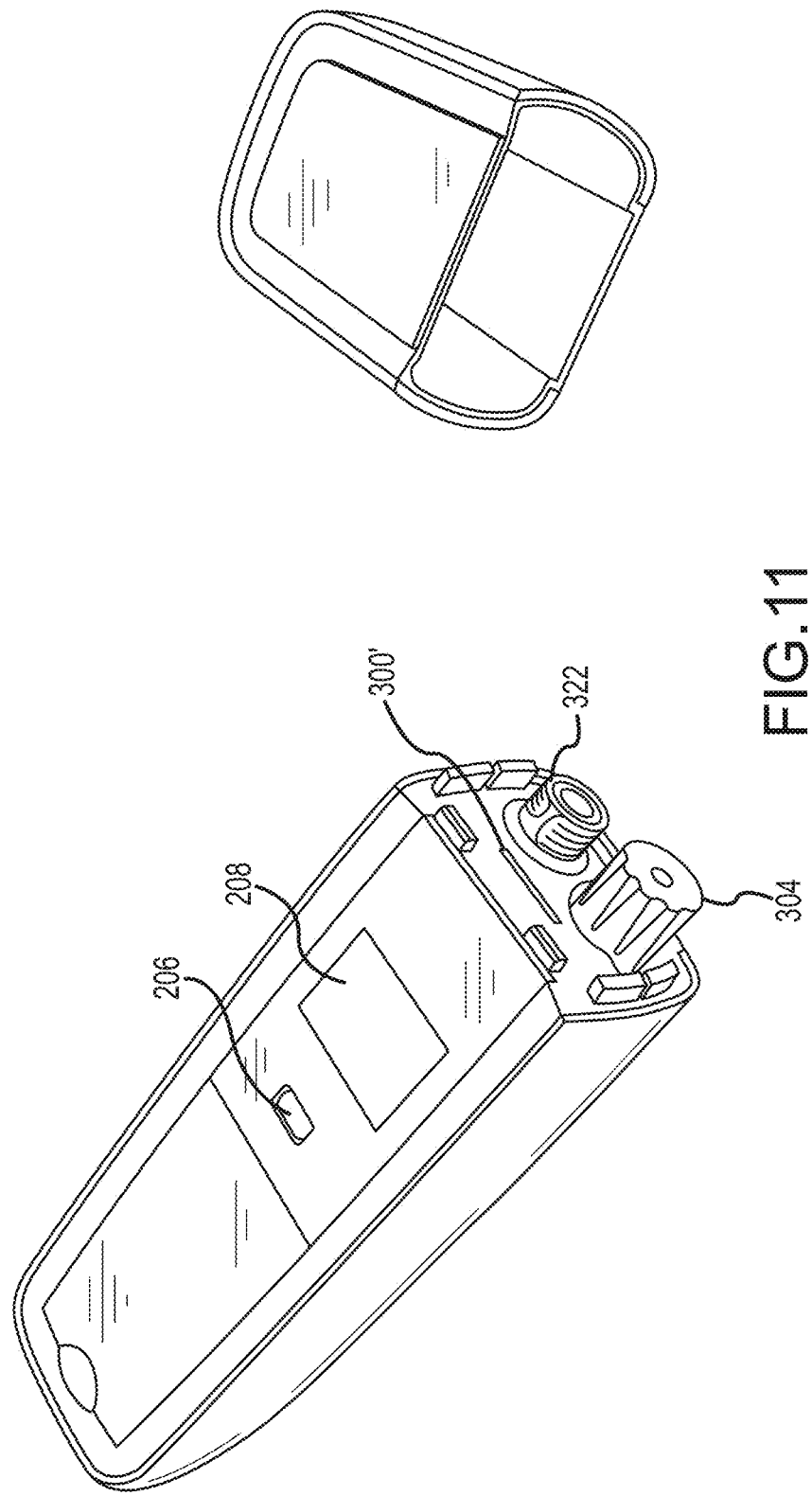
FIG. 11 is a perspective view of the embodiment of FIG. 2A showing the cap 200B removed from main body portion 200A.
Figure 12:
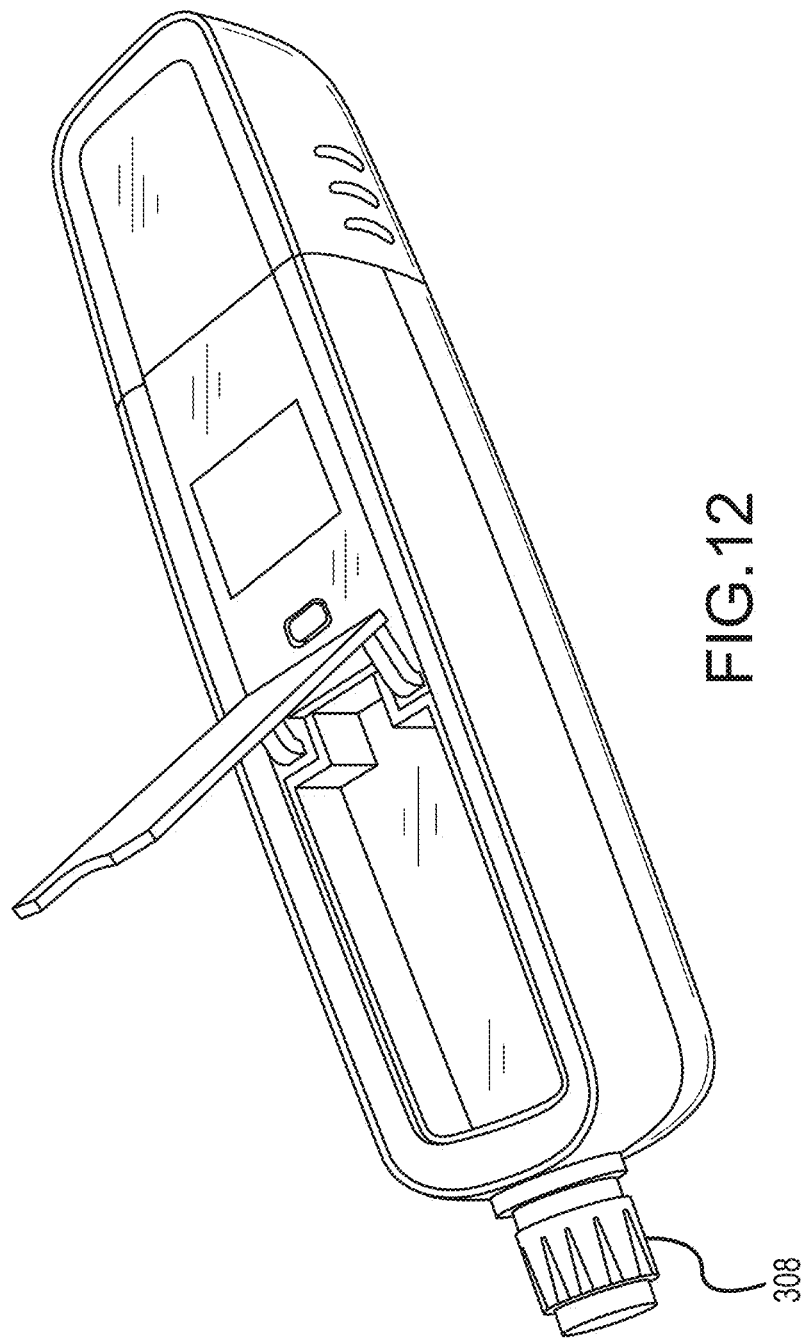
FIG. 12 is a perspective side view of the embodiment of FIG. 2A showing the top surface with the compartment open.
Figure 13:
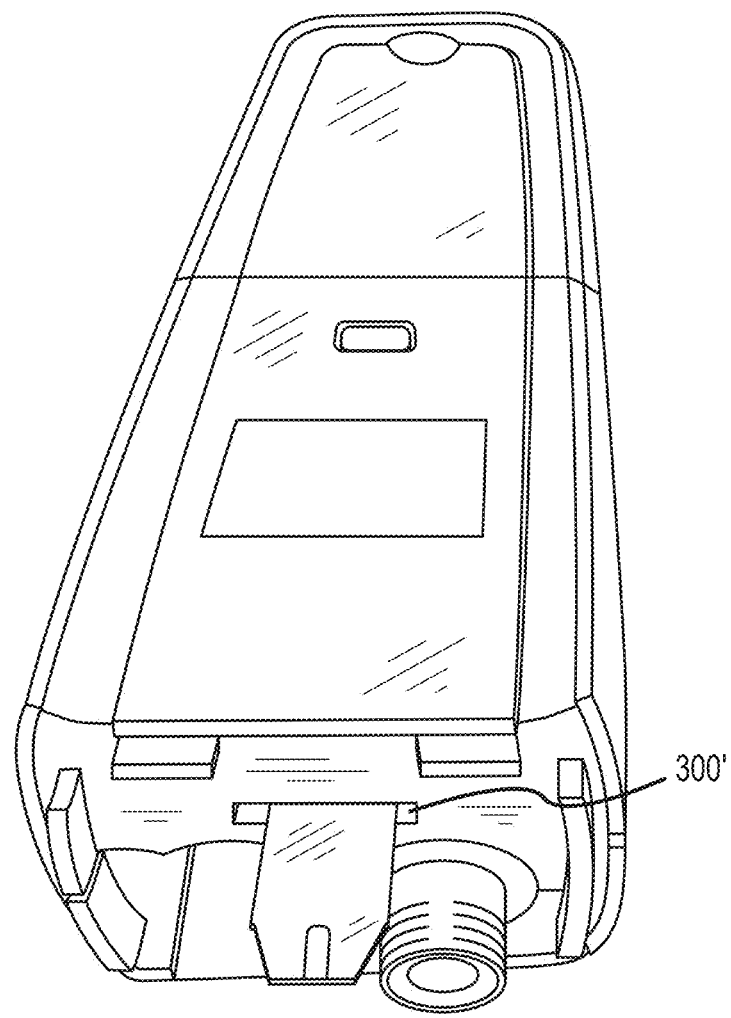
FIG. 13 is a perspective end view of the embodiment of FIG. 2A with a test strip inserted into the port.
Figure 14:
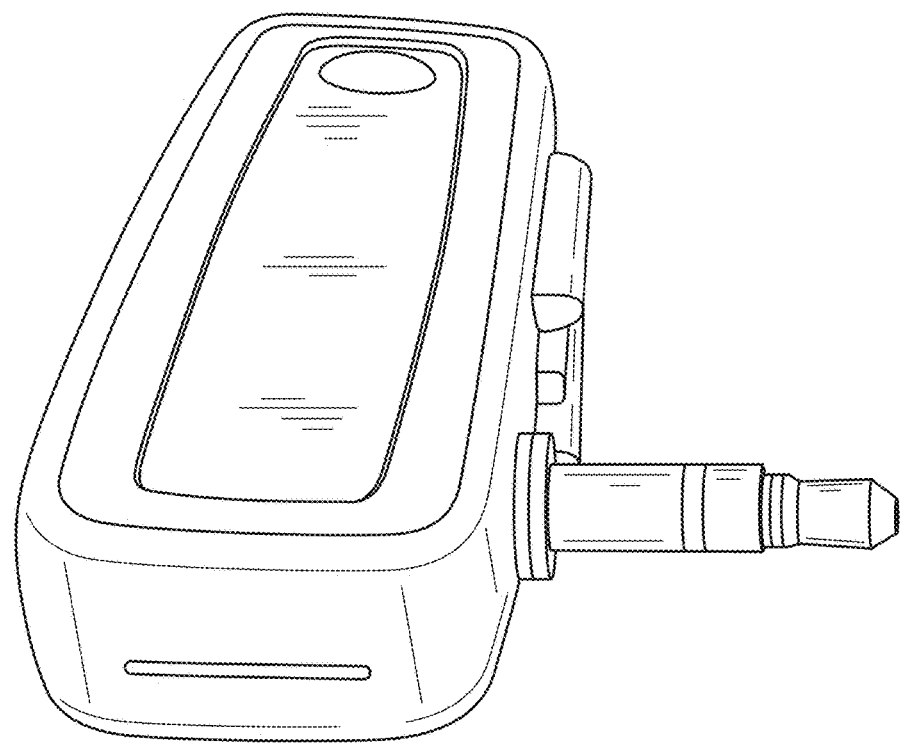
FIG. 14 is a perspective end view of an alternative embodiment of a device according to the invention showing a slot for insertion of a test strip and an audio jack to be received in a computing device.
Figure 15:
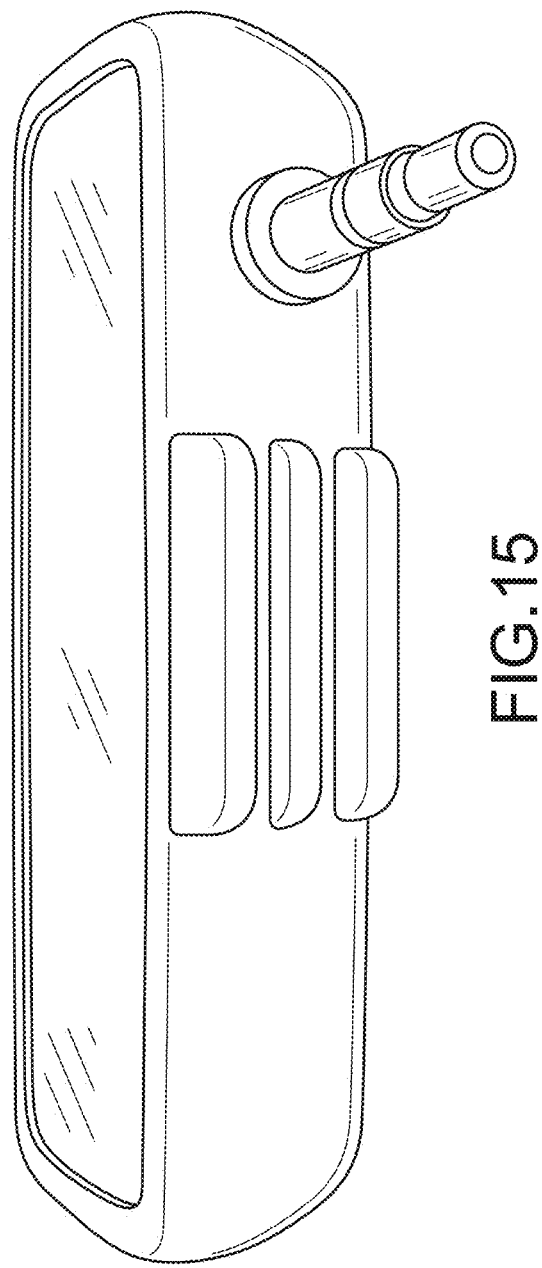
FIG. 15 shows the alternative embodiment according to FIG. 14 that has an audio jack that would plug into a computing device, such as a smart phone.
Figure 16:
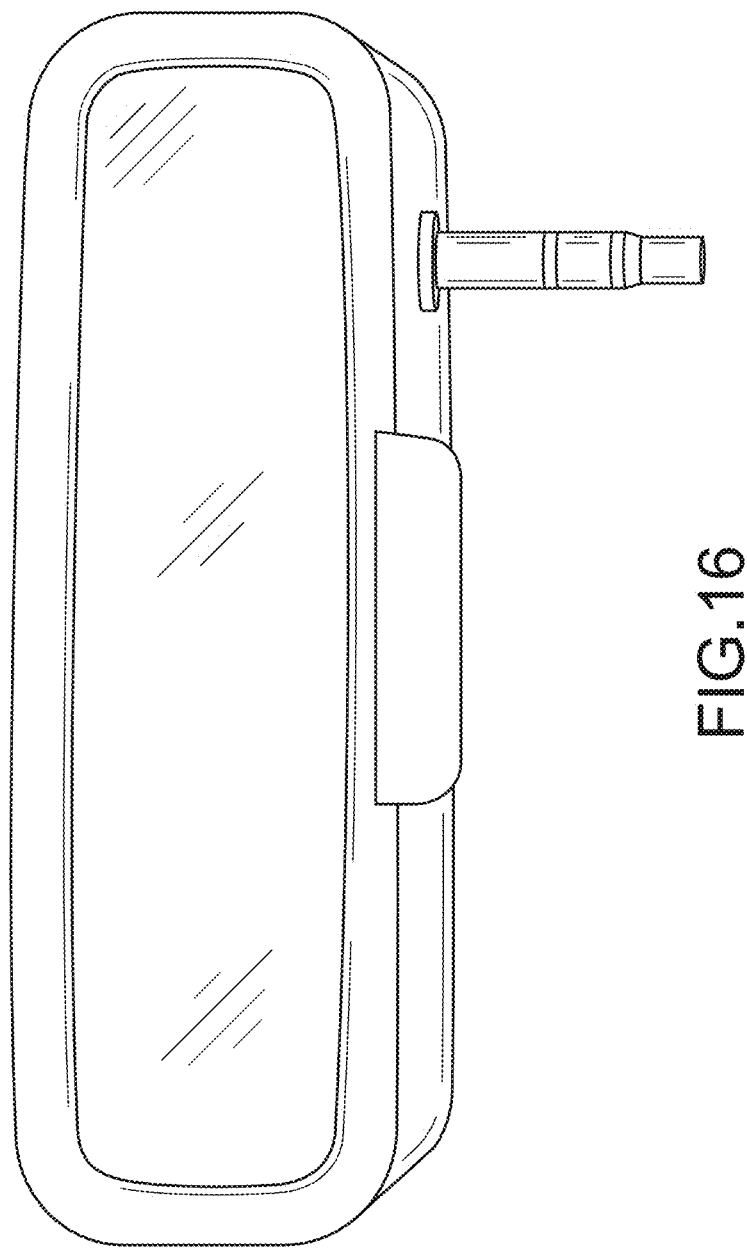
FIG. 16 is a top view of the device of FIG. 14.
Figure 17:
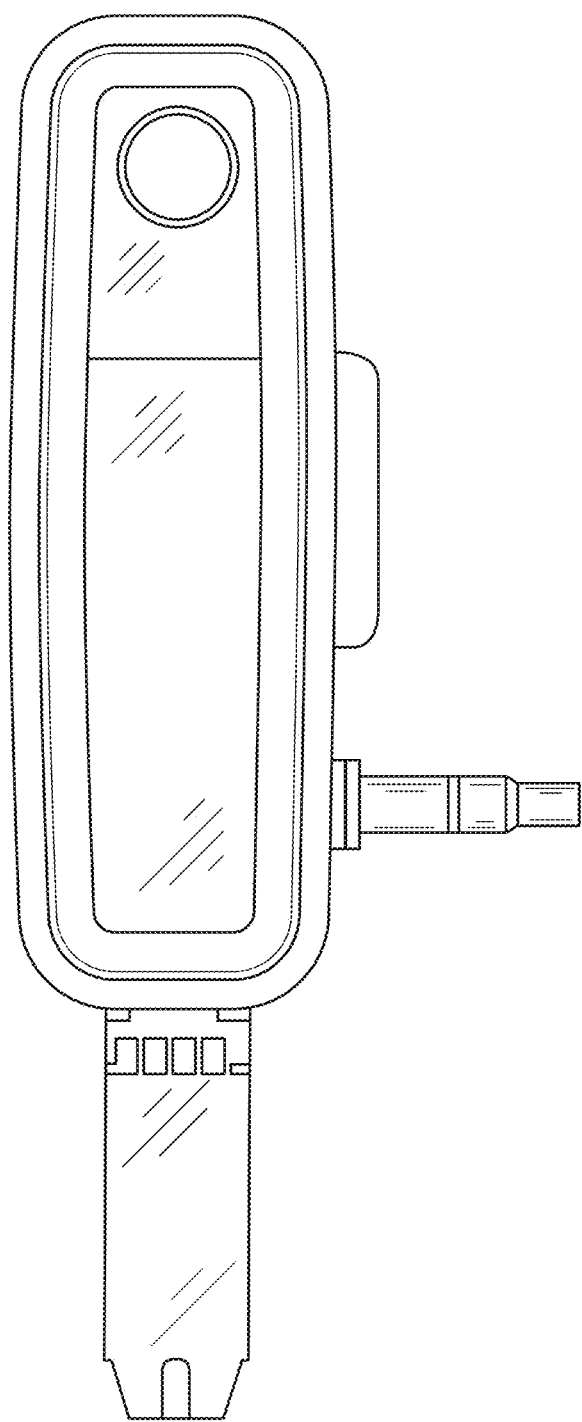
FIG. 17 is a bottom view of the device of FIG. 14.
Figure 18:
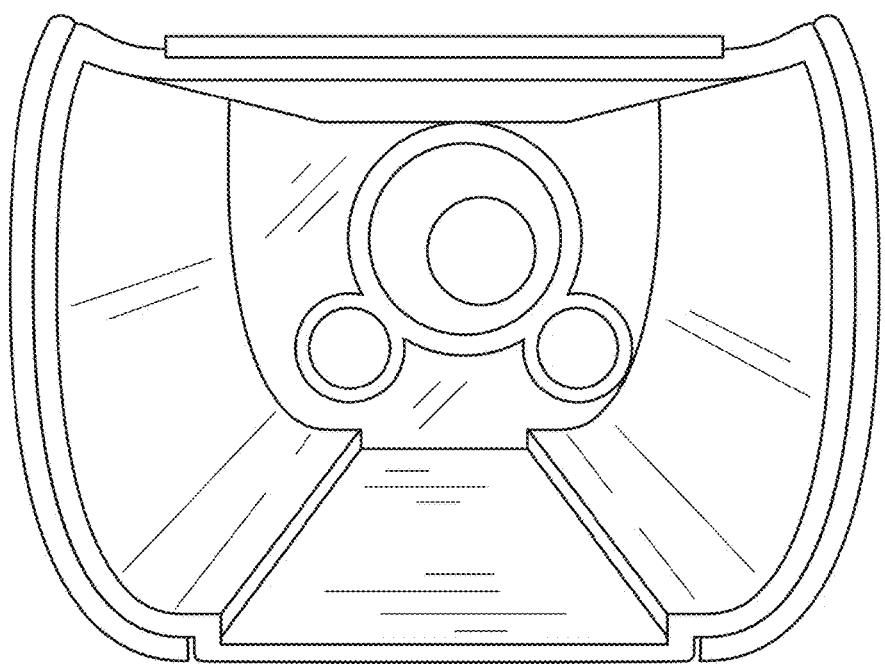
FIG. 18 is a cap according to aspects of the device showing one needle in the storage slot.

Assembly 200 may be stored in a cover 460 and worn on the clothing of the user, Cover 460 attach to the cover of the belt of the user as illustrated in FIG. 4F. Other figures that show illustrations of this embodiment are FIG. 5, which is a top view of kit 200 with a compartment door 201 partially open; FIG. 6, which is the second end 300 of device 200 and includes the second end 302 of the insulin pen (which receives a needle) and an opening to the lancet apparatus through which the lance exits to prick a finger, and the port or slot, which is an opening in the outer housing that leads to an opening in the meter; FIG. 7, which is the underside of device 200 and shows the button that releases the lance; FIG. 8, which shows an end view of device 200 and the insulin adjustment mechanism of the first end of the insulin pen; FIG. 9, which is a side, perspective view of device 200 showing its top surface; FIG. 10, which is a top view of device 200 showing the cavity door fully open; FIG. 11, which shows the cap removed from the second end 300; FIG. 12, which is a side, perspective view showing the cavity door fully open; FIG. 13, which shows second end 300 with a test strip inserted in the port; FIGS. 14-17, which show device 200 with an optional audio jack to plug into a computing device; and FIG. 18, which shows the cavity inside of the cap when removed from device 200.

When components are described as being "in communication" with each other in the detailed description or claims, such components may be in communication with each other constantly or periodically. Additionally, components in various embodiments may be in communication with each other via any suitable form of communication medium, use any suitable form of communication format, may be electrically coupled, physically coupled, and/or in communication with each other wirelessly.

EXEMPLARY SYSTEM

Figure 19:
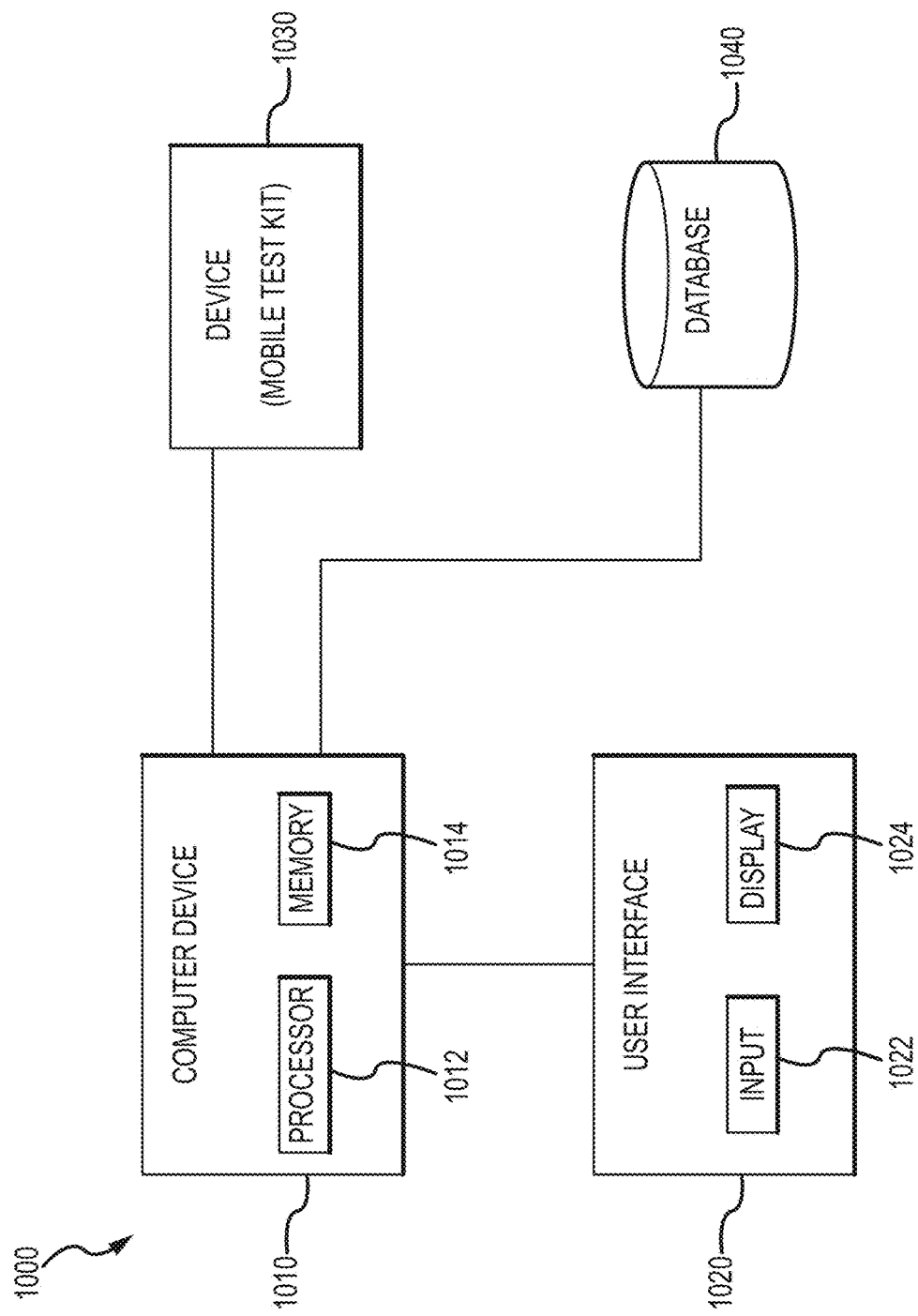
FIG. 19 illustrates an exemplary system according to various embodiments of the present disclosure.

An exemplary system 100 is depicted in FIG. 19. In various embodiments, the system 100 includes a computer device 110 comprising a processor 112 and a memory 114. Computer device 110 is in communication with a user interface 120, which includes an input component 122, and output component 124. In various embodiments, computer device 110 comprises any type of computing device, such as a smart phone, a tablet computer, a laptop computer, a desktop computer, a mobile subscriber communication device, a mobile phone, and/or a personal digital assistant (PDA). Computer device 110 may be further in communication with an external device 130, as well as a database 140.

Computer system 100 and other computing devices operating in conjunction with embodiments of the present disclosure may include an operating system (e.g., iOS, Windows, OS2, UNIX, Linux, Solaris, MacOS, etc.) as well as various conventional support software and drivers typically associated with computers. Software applications stored in the memory of such devices may be entirely or partially served or executed by the processor(s) in performing methods or processes of the present disclosure.

Figure 20:
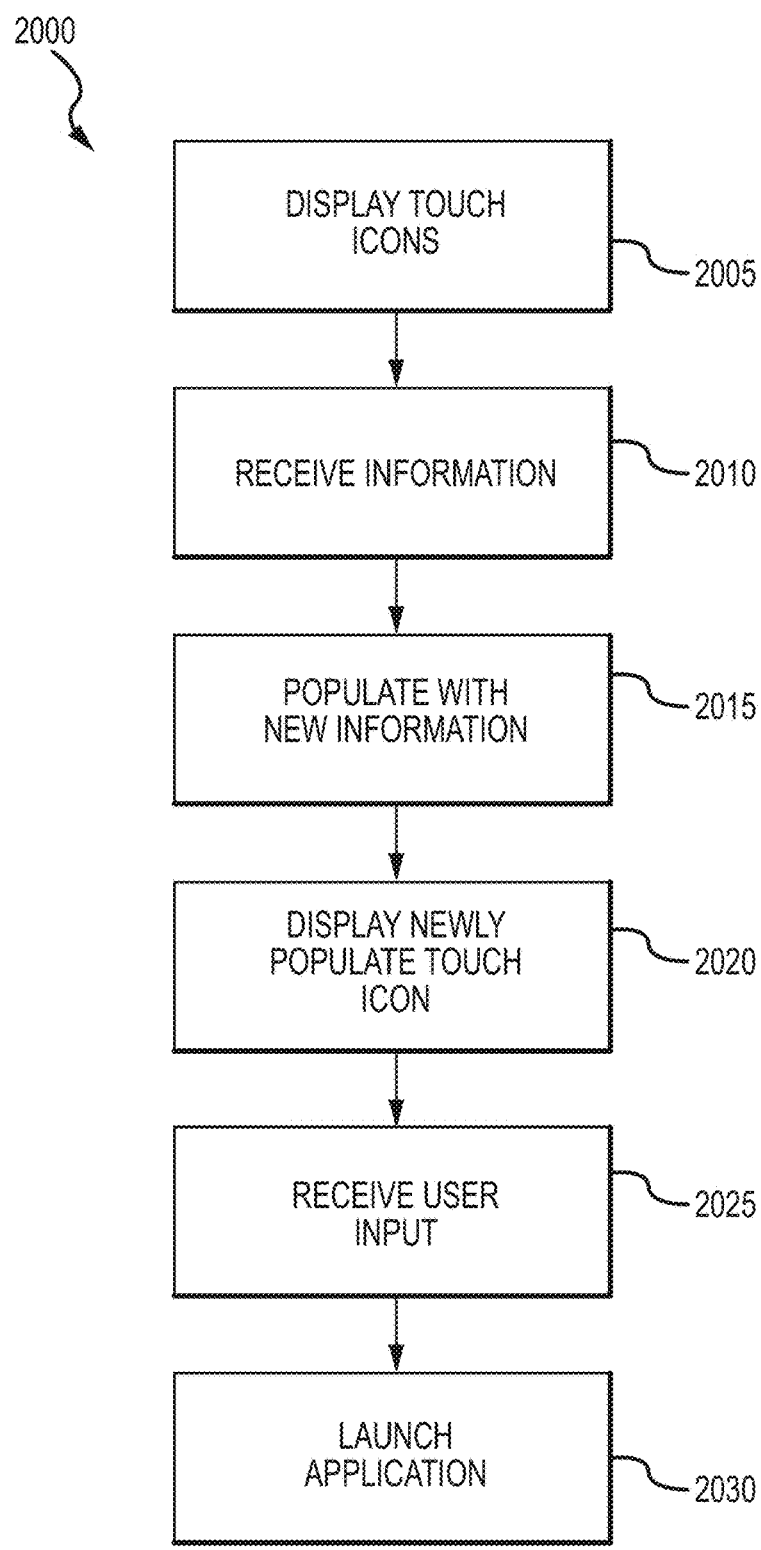
FIG. 20 is a flow diagram illustrating an exemplary process according to various embodiments of the present disclosure.

In various embodiments, and as shown in FIGS. 19 and 20, computer device 110 may store a software program configured to perform the methods described herein in the memory 114, and run the software program using the processor 112. Computer device 110 may include any number of individual processors 112 and memories 114. Various data may be communicated between computer device 110 and a user via user interface 120. Such information may also be communicated between computer device 110 and external device 130, database 140, and/or any other device connected to computer device 110 (e.g., through a local area network (LAN), or wide area network (WAN) such as the Internet).

In the exemplary system 100 depicted in FIG. 19, processor 112 retrieves and executes instructions stored in memory 114 to control the operation of computer device 110. Any number and type of processor(s) such as an integrated circuit microprocessor, microcontroller, and/or digital signal processor (DSP), can be used in conjunction with the embodiments described in the present disclosure. Processor 112 may include, or operate in conjunction with, any other suitable components and features, such as comparators, analog-to-digital converters (ADCs), and/or digital-to-analog converters (DACs). Functionality of embodiments of the present disclosure may also be implemented through various hardware components storing machine-readable instructions, such as application-specific integrated circuits (ASICs), field-programmable gate arrays (FPGAs) and/or complex programmable logic devices (CPLDs).

Memory 114 may include a non-transitory computer-readable medium (such as on a CD-ROM, DVD-ROM, hard drive or FLASH memory) storing computer-readable instructions stored thereon that can be executed by processor 112 to perform the methods of the present disclosure. Memory 114 may include any combination of different memory storage devices, such as hard drives, random access memory (RAM), read only memory (ROM), FLASH memory, or any other type of volatile and/or nonvolatile memory.

Computer device 110 may receive and display information (such as information related to a medical condition) via user interface 120. User interface 120 (and the user interfaces of any external device 130 used in conjunction with embodiments of the present disclosure) may include a screen display 124 or other peripheral output device 124 such as a monitor or printer, as well as any suitable input or control devices 122 (such as a mouse and keyboard) to allow users to control and interact with the software program.

User interface 120 may include any number of components, devices, and/or systems, such as speakers, an external memory device, a touch pad, a touch screen, and/or an alphanumeric keypad to allow a user to enter instructions, information related to their medical condition, and other input. User interface 120 may also include a microphone to allow a user to provide audio input, as well as a camera to allow the user to provide video input. Any of the components of the user interface 120 may be utilized as external devices 130 as described below.

The user interface of any component operating in conjunction with embodiments of the present disclosure may include, or operate with, audio or speech recognition software to process and analyze audio or verbal input through the user interface, as well as pattern recognition software to analyze graphics, text, and video received through the user interface 120, from external device 130, or from any other source.

Computer device 110 may communicate with any number of external devices 130. In some embodiments, one or more devices 130 are configured to obtain information regarding a medical condition and provide the information to computer device 110 through a wired or wireless connection. Devices 130 may also communicate directly with the database 140, each other, or with any other system or device operating in conjunction with the embodiments described herein.

A medical condition as managed by embodiments of the present disclosure includes any medical condition that can be tested and monitored on a periodic basis. As an exemplary medical condition, diabetes will be used as the medical condition managed by various embodiments of the present disclosure. However, any other medical condition that can be tested and monitored on a periodic basis (such as cholesterol, blood pressure, heart rate, sodium levels, potassium levels, creatinine levels, liver function) may also be monitored by embodiments of the present disclosure. Accordingly, embodiments of the present disclosure may operate in conjunction with external device 130 that includes a testing kit for detecting information about the medical condition and communicating it to computer device 110, database 140, or other system. External device 130 may communicate with computer device 110 or other device through a wired connection, such as a universal serial bus (USB) connection, an auxiliary port, a computer network connection, a mobile device synchronization port connection, a power connection, and/or a security cable. External device 130 may also communicate with any device operating in conjunction with an embodiment of the present disclosure through any desired wireless connection, such as a wireless Internet connection, a cellular telephone network connection, a CDMA/GSM/4G LTE network, a wireless LAN connection, a wireless WAN connection, and/or an optical connection.

Database 140 stores and provides information related to the medical condition, as well as any other desired information. Database 140 may be implemented on computer device 110 or hosted by another system or device (such as a server) in communication with computer device 100 via, for example, a network such as a LAN or WAN.

Computer device 110 and other computing devices operating in conjunction with embodiments of the present disclosure may include an operating system (e.g., iOS, Windows, OS2, UNIX, Linux, Solaris, MacOS, etc.) as well as various conventional support software and drivers typically associated with computers. Software applications stored in the memory of such devices may be entirely or partially served or executed by the processor(s) in performing methods or processes of the present disclosure.

Any of the components in FIG. 19, as well as other systems and components operating with, or as part of, embodiments of the present disclosure may communicate with each other via a network (not shown). In some embodiments, one or more components of system 100 may include a wireless transceiver and the network may comprise a wireless system to allow wireless communication between various systems and devices, such as a wireless mobile telephony network, General Packet Radio Service (GPRS) network, wireless Local Area Network (WLAN), Global System for Mobile Communications (GSM) network, Personal Communication Service (PCS) network, Advanced Mobile Phone System (AMPS) network, and/or a satellite communication network. Such networks may be configured to facilitate communication via any other type of connection, such as a wired Internet connection, a wireless Internet connection, a cellular telephone network connection, a CDMA/GSM/4G LTE network, a wireless LAN connection, a wireless WAN connection, an optical connection, a USB connection, and/or a mobile device synchronization port connection.

Exemplary Methods

The methods described below may be implemented in any manner, such as through a software program operating on a computer-based system. Such a software program may be stored on any computer-readable medium, such as floppy disks, hard disks, CD-ROMs, DVDs, any type of optical or magneti-optical disks, volatile or non-volatile memory, and/or any other type of media suitable for storing electronic instructions and capable of interfacing with a computing device. Methods according to embodiments of present disclosure may operate in conjunction with any type of computer system, such as a smart phone, personal computer (PC), server, cellular phone, personal digital assistant (PDA), portable computer (such as a laptop), embedded computing system, and/or any other type of computing device. The system may include any number of computing devices connected in any manner, such as through a distributed network. The system may communicate and/or interface with any number of users and/or other computing devices to send and receive any suitable information in any manner, such as via a local area network (LAN), cellular communication, radio, satellite transmission, a modem, the Internet, and/or the like.

Exemplary embodiments of this disclosure provide for an application that runs on computer device 110 and allows the user to interactively track historical data and information about each blood sugar test and result. The application will also store information about meals and perform an analysis of that data. The user and medical professionals can log into a web application and track progress and adjust the user's treatment plan as necessary. The system will alert the user and medical professionals of issues and irregularities. The application will allow the user to provide information about additional test results such as A1 test results.

FIG. 20 depicts an exemplary method according to various aspects of the present disclosure, and may be used with any suitable system, including the system 100 depicted in FIG. 19. The method in FIG. 20 may be practiced with more, fewer, or different steps in conjunction with various embodiments of this disclosure, and may be performed by hardware, software, or a combination of the two as described above. The steps in FIG. 20, as with the steps in the methods shown in the other figures may be combined with each other in any suitable order in accordance with various embodiments of the present disclosure.

Figure 21:
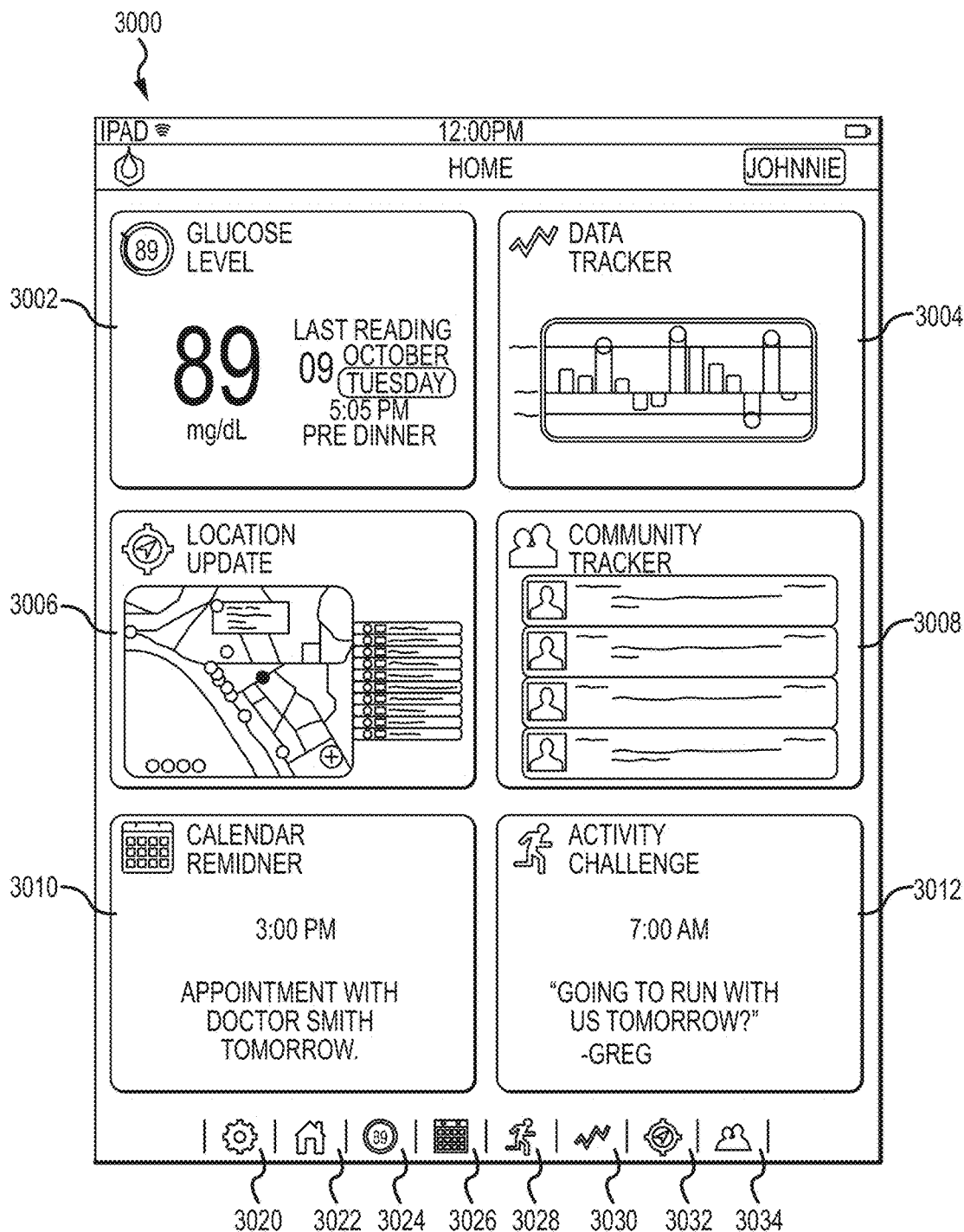

As shown in FIGS. 20 and 21, exemplary method 200 includes displaying, on display screen 300, a plurality of touch icons displaying information related to the medical condition such as diabetes (step 205), and receiving information relating to the medical condition (step 210). In response to receiving new information, method 200 also includes automatically populating one or more of the touch icons with the new information relating to the medical condition (step 215) and displaying the newly populated touch icon on display screen 300 (step 220). Method 200 additionally includes receiving user input in the form of a touch, key pad entry, or other input indicating selection of one of the touch icons (step 225). Method 200 further includes launching an application associated with the selected touch icon (step 230), as will be described below.

With reference to FIG. 21, an example of a screenshot is illustrated that shows a plurality of touch icons displayed on display screen 300 upon launching an application for the management of a medical condition such diabetes. In this embodiment, the plurality of touch icons include a glucose level window 302, a glucose tracking window 304, a location update window 306, a community tracker window 308, a calendar window 310, and an activity challenge window 312.

Figure 22:
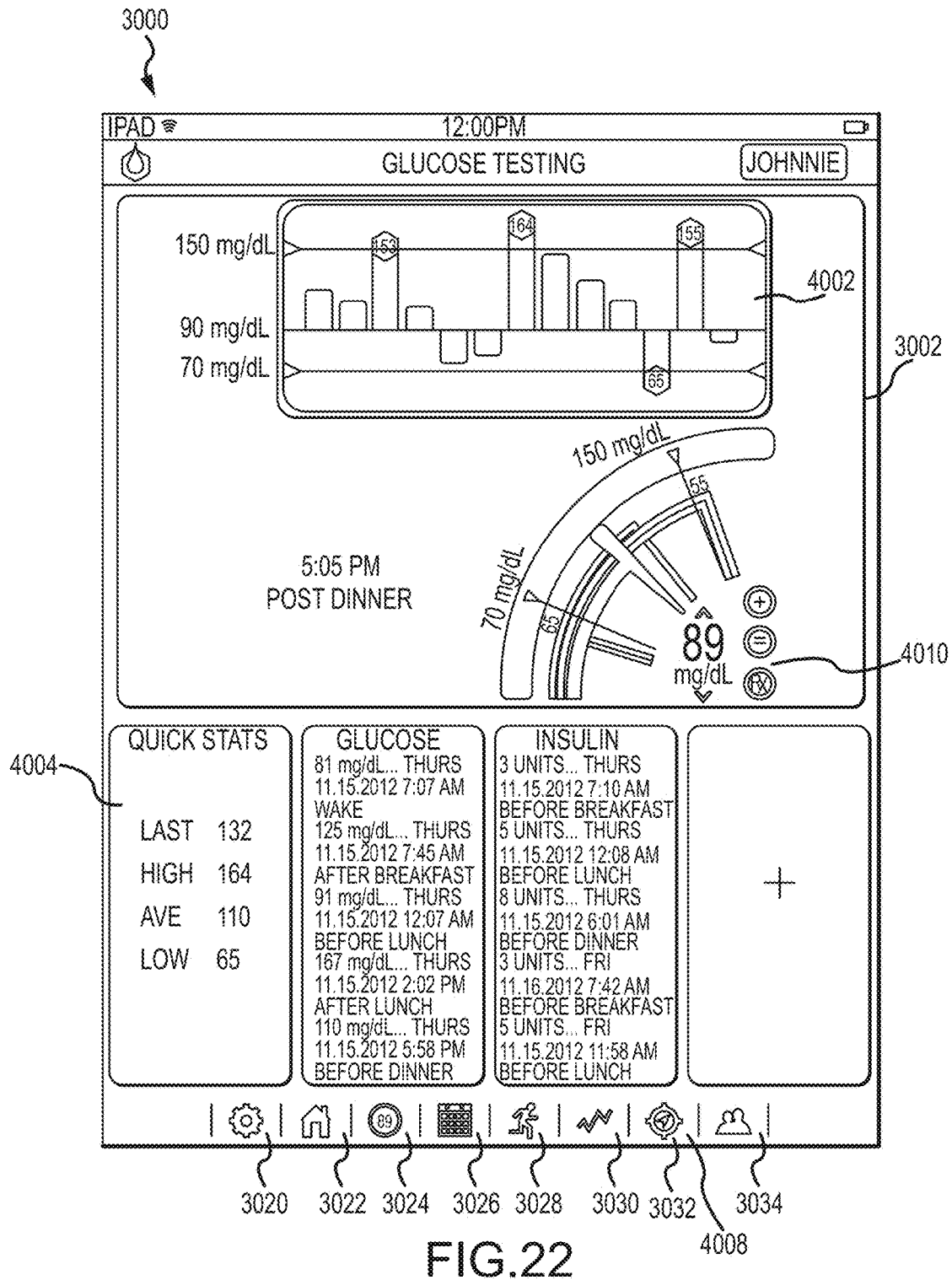

In an exemplary embodiment, there will be a row of one or more small icons 320-334 located on an edge of display screen 300. Small icons 320-334 may be located on any edge of the display screen, for example, the bottom edge, and the small icons will always be displayed, even when an application for one of the touch icons is launched, as illustrated in FIGS. 22-25. Each of touch icons 302-312 has a corresponding small icon 324-334 located on display screen 300. With reference to FIG. 22, icon 324 corresponds to glucose level window 302. Icon 326 corresponds to calendar reminder window 310. Icon 328 corresponds to activity challenge window 312. Icon 330 corresponds to glucose tracking window 304. Icon 332 corresponds to location update window 306, and icon 334 corresponds to community tracker window 308. When one of small icons 324-334 is pressed, or otherwise activated by the user, the application for the touch icon that corresponds to the selected small icon is launched. In addition to the small icons that correspond to the touch icons, addition small icons may be displayed, such as small icon 320 that can be used to launch a settings or tools application, and small icon 322 that can be used to return to the home or initial screen display.

Glucose level window 302 shows the blood glucose level of the last recorded blood test. The blood glucose level can be displayed with a color coded scheme to show high (e.g., red), low (e.g., blue), and normal (e.g., green) readings. When the user takes a new blood test with a portable testing kit 120 that is in communication (via wireless or wired connection) with computer device 110, the glucose level in window 302 is updated to show the results of the latest blood test.

Figure 23:
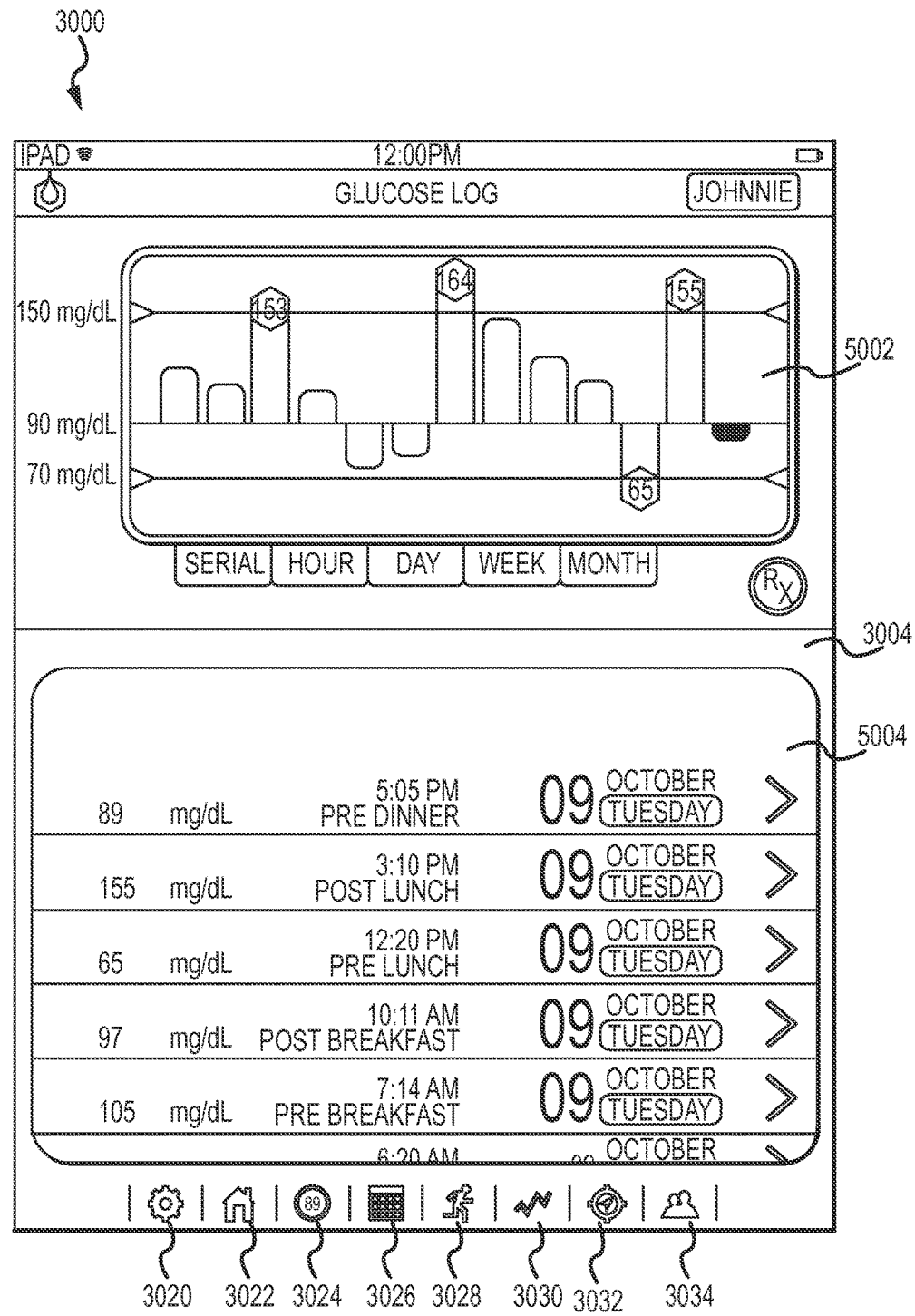

With reference to FIG. 23, when the application associated with glucose level window 302 is launched, by, for example, touching or otherwise activating its touch icon or small icon 324, the glucose level window is displayed so that it fills the entire display screen 300. The displayed information includes the most recent blood glucose level that was recorded, along with historical data 402 that shows current and past blood glucose levels distributed around target ranges. The data can be displayed with color coding, so that levels above the high target range are displayed in the color chosen by the user to represent high readings, such as red. Levels below the low target range are displayed in the color chosen by the user to represent low readings, such as blue. Levels between the two high and low target ranges are displayed in the color chosen by the user to represent normal readings, such as green. Additional information is displayed such as statistics 404 for last, high, average, and low blood glucose levels. In addition, information for previous blood glucose tests (406) and previous insulin injections (408) is displayed. In the example illustrated in FIG. 23, the previous five blood glucose tests and the previous five insulin injections are displayed.

A Rx icon 410 is displayed that allows the user to track previous insulin injections in more detail. If the user touches or otherwise activates Rx icon 410, insulin information 408 is expanded to fill the display screen with information displayed for all previous insulin injections.

Glucose tracking window 304 shows past test results fluctuating around one or more target lines or ranges. When the user takes a new blood test with portable testing kit 120 that is in communication (via wireless or wired connection) with computer device 110, the test results displayed in glucose tracking window 304 are updated to show the results of the latest blood test.

Figure 24:
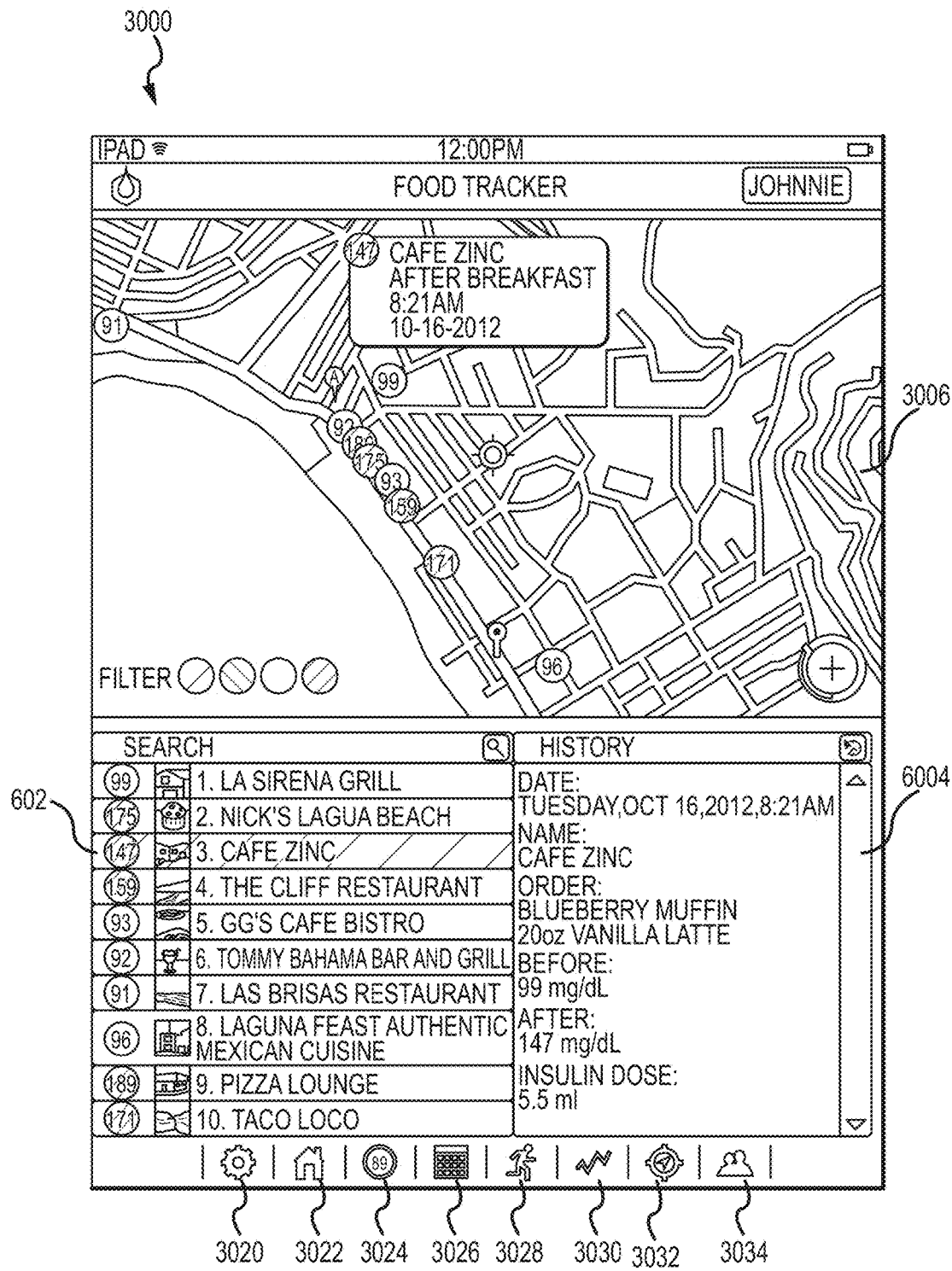

With reference to FIG. 24, when the application associated with glucose tracking window 304 is launched, by, for example, touching or otherwise activating its touch icon or small icon 330, the glucose tracking window is displayed so that it fills the entire display screen 300. The displayed information includes historical data 502 that shows current and past blood glucose levels distributed around target ranges. The data can be displayed with color coding, so that levels above the high target range are displayed in the color chosen by the user to represent high readings, such as red. Levels below the low target range are displayed in the color chosen by the user to represent low readings, such as blue. Levels between the two high and low target ranges are displayed in the color chosen by the user to represent normal readings, such as green. The displayed historical data can be filtered so that the data is displayed on an hourly, daily, weekly, or monthly basis. Alternatively, the historical data can be displayed in a serial manner, so that the most recent blood glucose levels are displayed. Additional information is displayed such as statistics 504 for previous blood glucose tests. The displayed information includes blood glucose level in a color coded scheme to show high/normal/low levels, date/time of test, including whether the test was before or after a meal, and the time elapsed between a meal and the test results.

Location update window 306 shows a user's glucose levels at various locations. Information from the user's previous meals and blood sugar test results at various locations is used to provide reminders about meals and blood sugar testing levels at a specific location. The user will be notified when the device's global positioning system (GPS) recognizes a previous location that was visited by the user.

Figure 25:
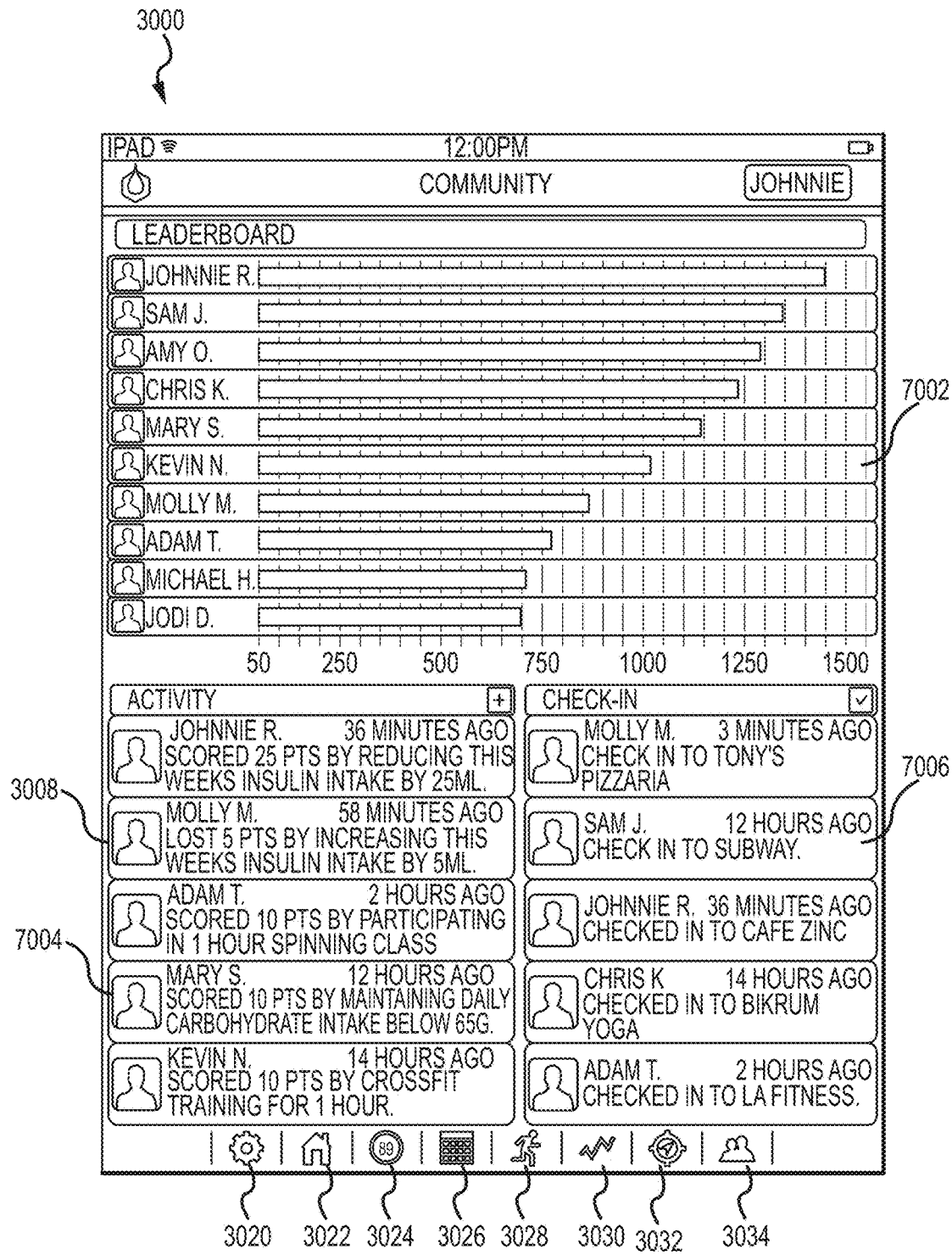

With reference to FIG. 25, when the application associated with location update window 306 is launched, by, for example, touching or otherwise activating its touch icon or small icon 332, the location update window is displayed so that it fills the entire display screen 300. The displayed information includes a map with color coded push pins showing various locations visited by the user. For example, if the user's average blood sugar level at a specific location for all visits is above their target range, then the color coded push pin will be displayed with a color (e.g., red) that indicates the user's high average blood sugar level at that location. Alternatively, if the user's average blood sugar level at that location for all visits is below their target range, then the color coded push pin will be displayed with a color (e.g., blue) that indicates the user's low average blood sugar level at that location. If the user's average blood sugar level at that location for all visits is within their target range, then the color coded push pin will be displayed with a color (e.g., green) that indicates the user's normal average blood sugar level at that location. The display may be filtered by the color coding so that all push pins are displayed, only high blood sugar level (e.g., red) push pins are displayed, only normal blood sugar level (e.g., green) push pins are displayed, or only low blood sugar level (e.g., blue) push pins are displayed.

The user can use search window 602 to search and display information on specific locations. The application will display all previous visits to a specific location in chronological order, with the most recent visit displayed on top. In addition, the application will display the date/time and meal information, along with an optional photograph. This information will provide the user with a reminder of what they ate and the impact the meal had on the user at the time of their blood testing. In addition, the system will notify the user to take a blood test in standard time intervals after a meal and/or before a meal, in order to keep the user on track with regularly scheduled blood tests.

The information that is provided to the user by the application associated with location update window 306 will allow the user to make better decisions about new meals at the same location. As an example, when the user enters a location, the application will display and/or state the user's average blood sugar level at that location. In addition, the application can turn the background of display screen 300 to a color that represents the overall impact to the user's blood sugar level of the meals eaten at that location. In time, and after the user provides meal information and blood sugar levels for a variety of locations, the system will display a map that will enable the user to see locations that promote good diabetic management and those locations that promote poor diabetic management. In an exemplary embodiment, the user will be able to hold a camera that is an internal or external peripheral of computer device 110, and when the user points the camera up and down a street with a row of restaurants, the system will display the user's average blood sugar results at each location.

Figure 26:
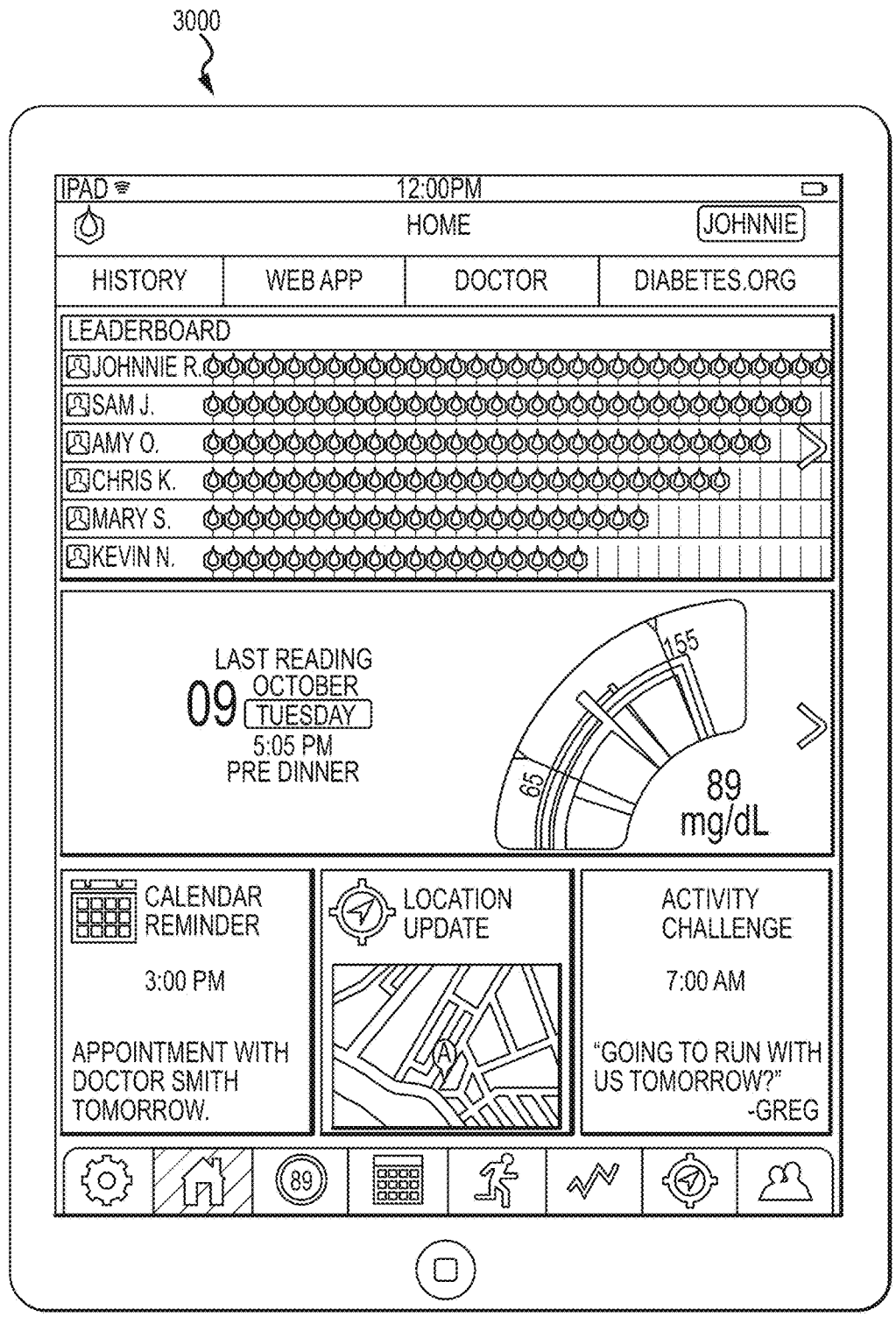
Figure 27:
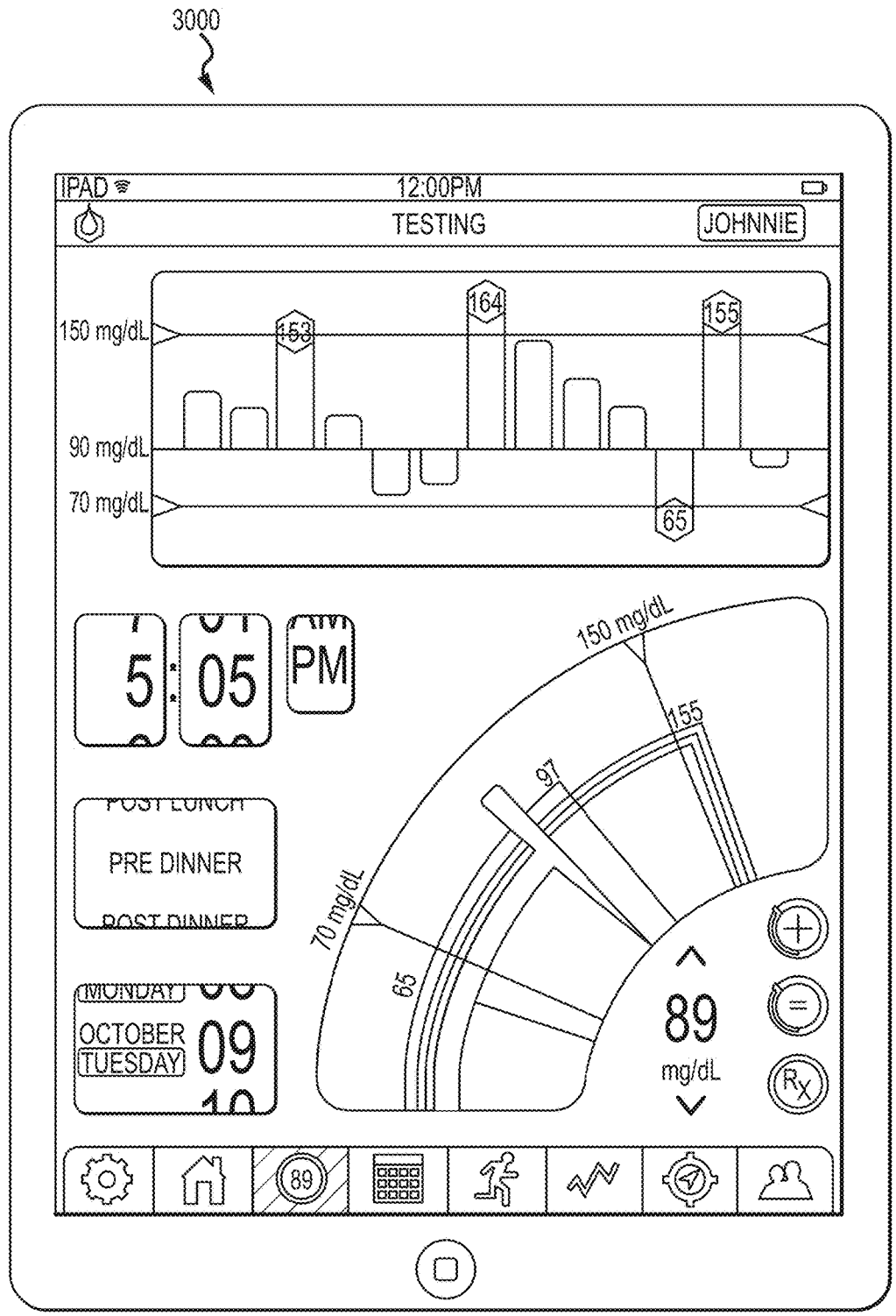
Figure 28:
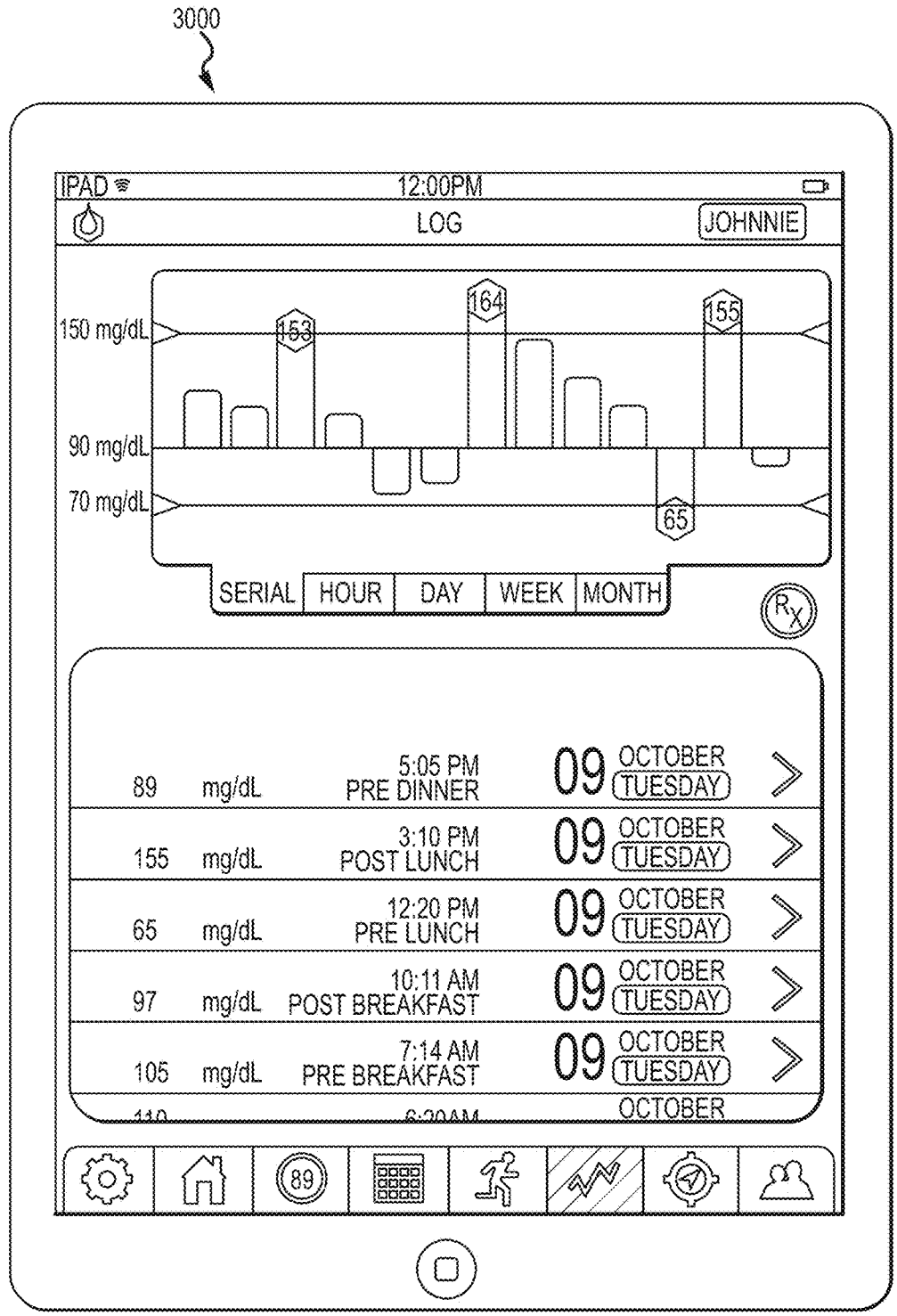
Figure 29:
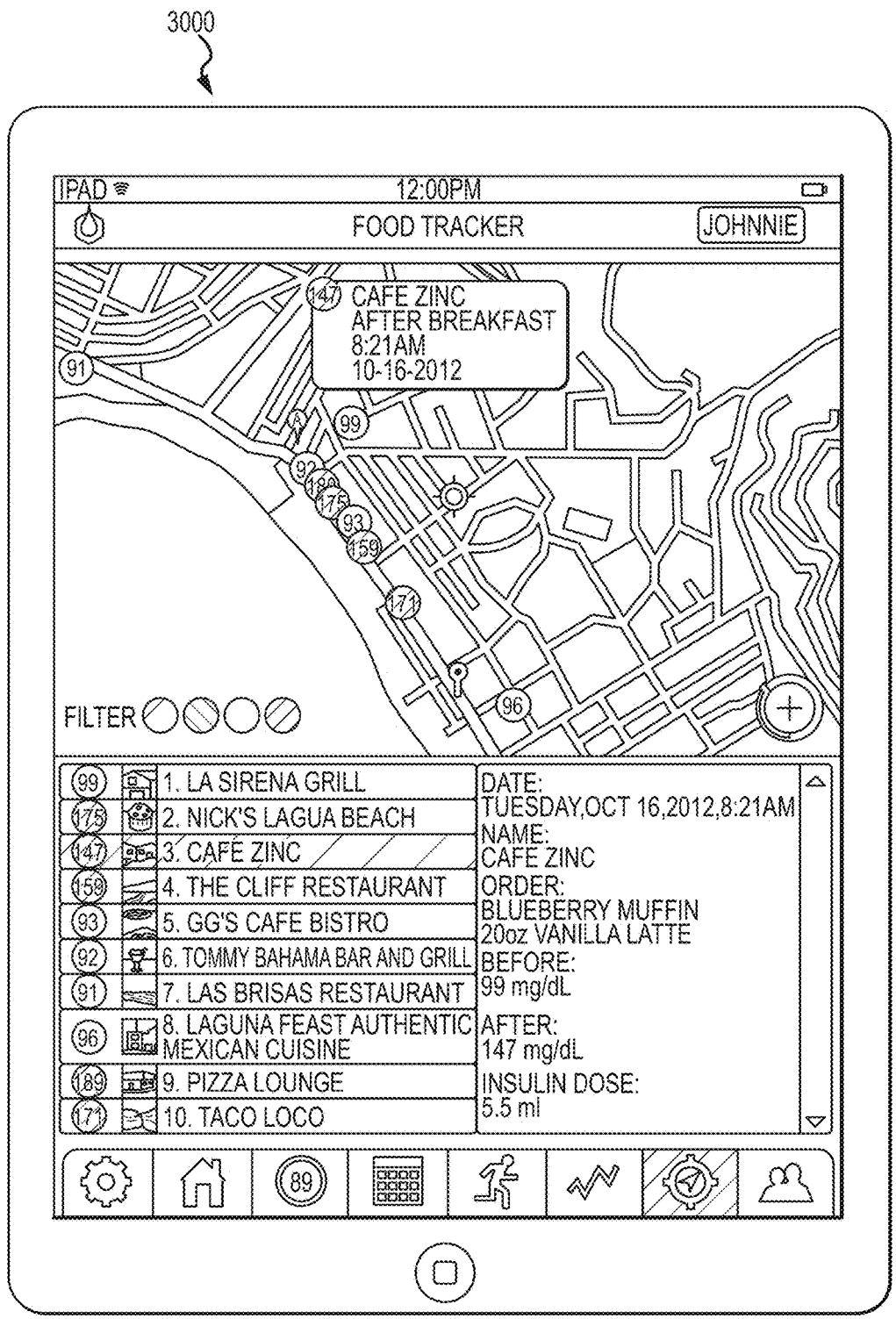
Figure 30:
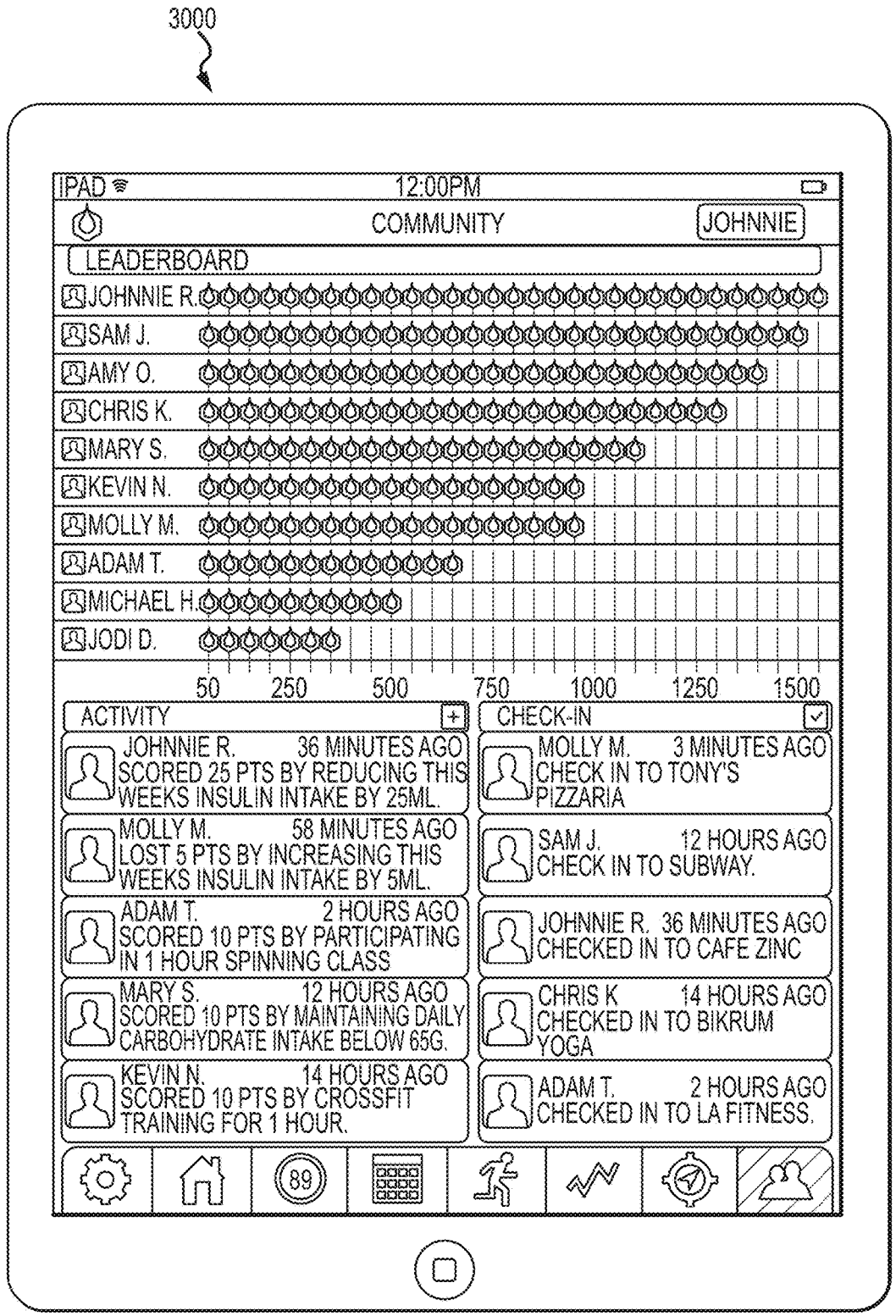
Figure 33:
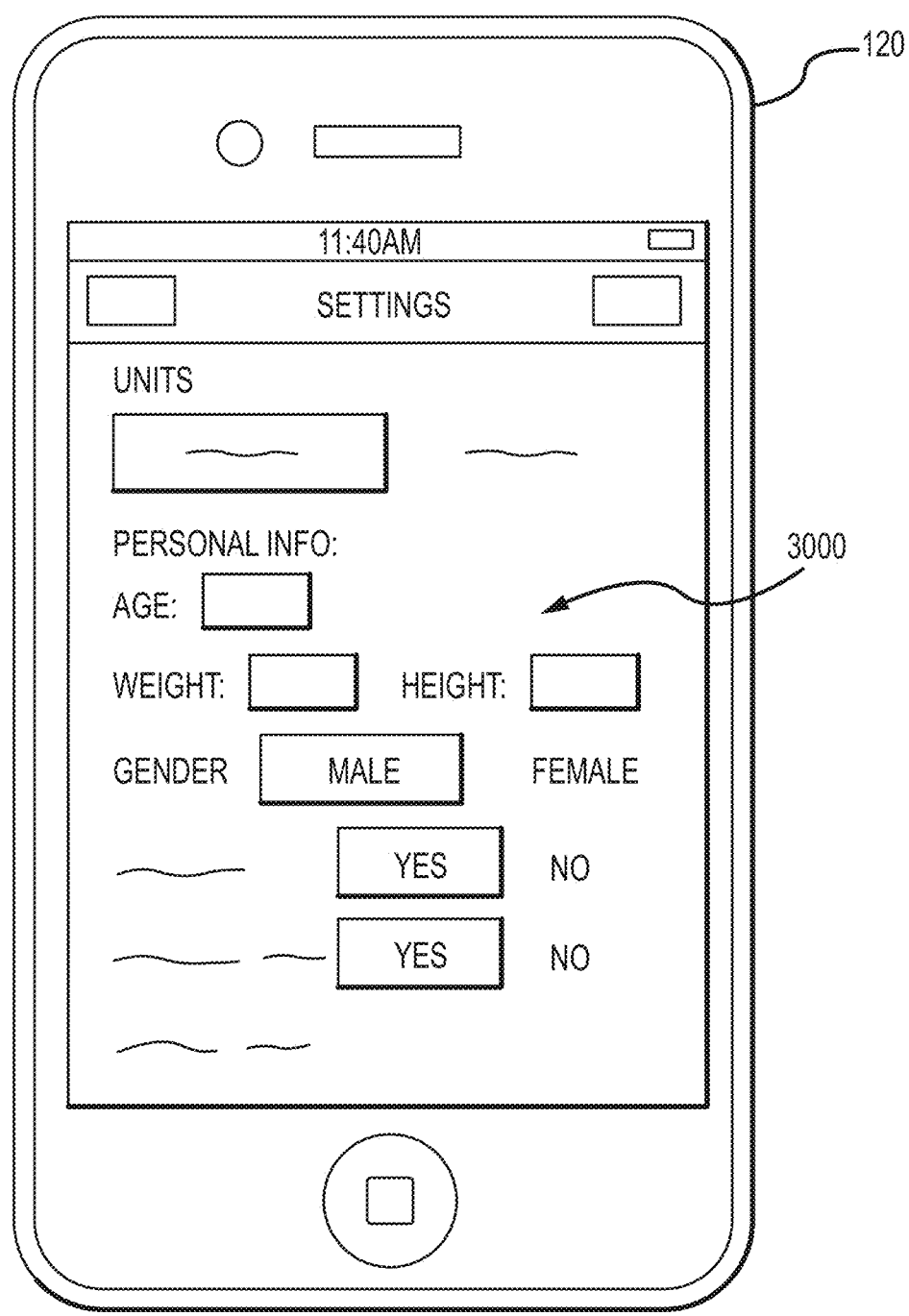
Figure 34:
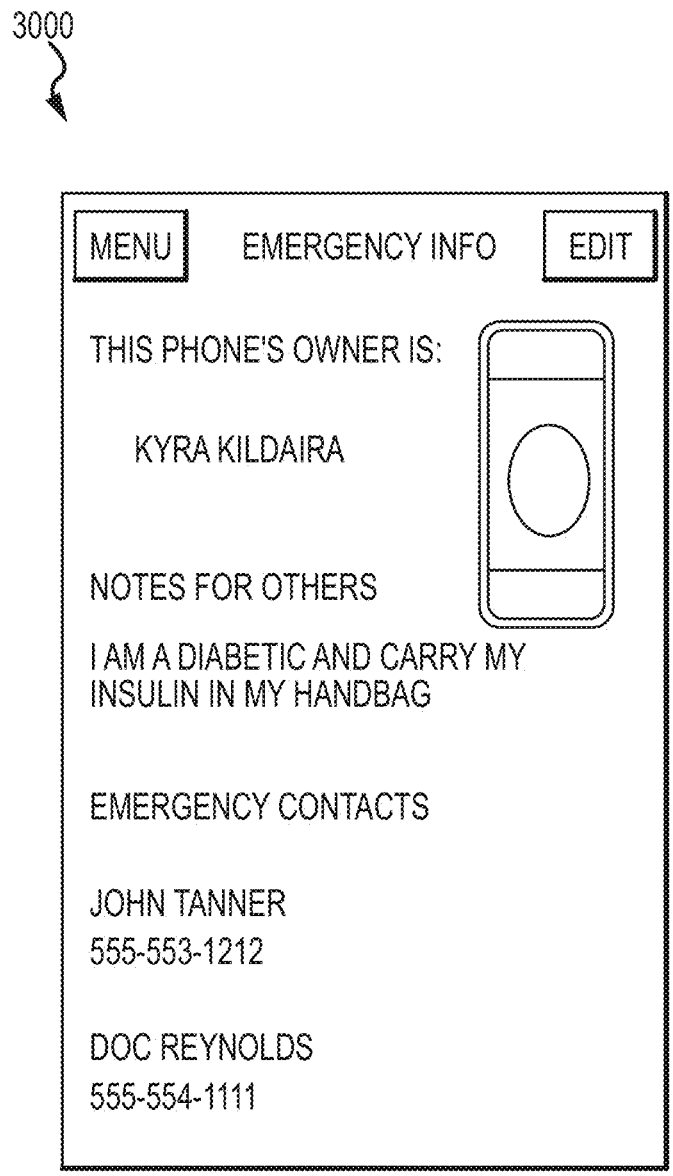

Community tracker window 308 shows the activity of other people in the user's community. With reference to FIG. 26, when the application associated with community tracker window 308 is launched, by, for example, touching or otherwise activating its touch icon or small icon 334, the community tracker window is displayed so that it fills the entire display screen 300. The displayed information includes leaderboard 702 that shows the points earned and lost by the user and other people in the user's community for certain activities such as reducing insulin intake (earn points), increasing insulin intake (lose points), exercise (gain points), maintaining diet (earn points), and not maintaining diet (lose points). The displayed information can include chat board 704 where the user and other people can record their activities and/or comments. Additional information can be displayed in check-in window 706 that shows recent locations, such as restaurants and exercise facilities, for people in the user's community.

In an exemplary embodiment, the application associated with community tracker window 308 allows the user to interface with other people in various topics such as diet, stress control, carbohydrate intake, exercise, medication (include side effects and benefits), and in an open discussion forum. The user will also be able to seek information from medical professionals to answer questions and provide advice. The user will also be able to add information about their own doctor(s) such as address, contact information, and past medical results and keep that information private to the user. In addition, the system will allow the user to set up parameters provided by their doctor for blood sugar levels, when fasting, and for after meals. If an average weekly or monthly range is surpassed, the system can notify the user's doctor via e-mail or other contact method that the user is over the acceptable range and needs an appointment to review their results.

Calendar reminder window 310 allows the user to view information about various events on their calendar including doctor appointments, meals/locations, and blood sugar test results. In exemplary embodiments, the user can visually review their blood sugar results for the past few days, weeks, or months. This information may be provided to the user graphically for ease of viewing. For example, when the user selects a month, the color of the days within the month will indicate whether the user's blood sugar levels were poor, moderate or good. The user can click on a particular day to see what and where they ate.

Activity challenge window 312 shows an activity that is updated on a periodic basis, such as daily, and is used to challenge the user. For example, another person might challenge the user to run or go for a walk on a particular day.

In exemplary embodiments of the present disclosure, the user creates an account with the system by entering an account name, such as a valid e-mail address, and a password. For initial setup, the user can enter personal information such as age, race, A1C levels and dates of test, daily testing times and reminders for testing. In addition, the user can select a color scheme that appeals to the user such as: a choice of green or blue for positive information, a choice of orange or yellow for modest or warning information, and a choice of red or black for negative or poor results.

After the initial setup, when the user logs into the system by launching the application and entering their account name and password, the plurality of touch icons 302-312 is displayed on display screen 300. The system will process the history of past test results and compile the results for display in the touch icons. The user will be able to set the range of history that is used for the displayed results. In an exemplary embodiment, the user will be able to set the range of history to the past twenty four hours, the past week, or the past month. The system will turn the background color of display screen 300 to reflect the past results (e.g., green if the past results are all positive) and alternatively, announce (e.g., via Siri on an iPhone), how the user is doing.

The system can use the device or information available via a network such as the Internet to determine the date and time for the announcement. As an example, upon launching the system application, display screen 300 will turn green or blue (depending on the user selection) and the system will cause the device to state and/or display: "Good morning 'Johnnie' (or other user name). Your blood sugar levels are in good shape today." Or, for a different time of day with poor results, display green 300 will turn red or back and the system will cause the device to state and/or display: "Good evening 'Johnnie' Your blood sugar levels have gone above acceptable ranges. Please ensure to take immediate action." Then, depending upon the user's setup for the system, the system will remind the user to test their blood sugar again, within a set time period, such as one or two hours to ensure that their blood sugar level is back within tolerable range.

EXAMPLE 1

The following is one example of how an electronic, computer system and method could function according to the invention.

Main Screen:

In this example, the software is either loaded onto a mobile device or computer, is downloaded from a server when a request is sent, or operates on a separate server. Preferably, an icon for the software application is visible on a home screen of any suitable device or computer.

In this example, when a user clicks on the icon the screen first goes black and a clear white sugar cube slowly resolves and becomes granular looking. It then tilts on a slight angle and a small drop of red blood will appear and slowly get larger until it drips off the lower right corner of the cube down the screen and highlights the log-in button in red. During this time the software, if not permanently loaded onto the hard drive of the device, will load from a remote source, such as a server accessible via the internet.

The user must then log into the application with a valid email address and password. This will also create an account for the user, if the user does not already have an account.

Once the log in is completed, the application opens up on the settings page. At that point, the user can enter personal information such as: Age; race; A1C levels and dates of test; daily testing times and reminders for testing. The user may also select a color scheme that appeals to him/her, such as: green or blue for positive results; orange or yellow for modest or mild results; and red or black for negative or poor results.

The next aspect of this example of the application is the greeting screen. After the initial set up, when a user logs into the application, the system will review the history of the user's test results and compile the results to inform the user of his/her average results. The user may set the time range of his/her history, for example, as follows:

The past 24 hr. testing results (e.g., 4 test results average a BS of 130). The past week (e.g., average BS of 145) or the past month (e.g., average BS of 125). A user may select one time frame at a time or view them in a single frame.

The application background may turn color to reflect the past results and announce (such as via Siri fxn) in a voice how the user has done.

Next, the application can determine the date and time for announcements, such as set forth in the following example:

Ex. 1: the screen turns green or blue and states: "good morning Johnnie Your BS levels are in good shape today."

Ex 2: the screen turns red or black and states: "Good evening Johnnie Your BS levels have gone above acceptable ranges please ensure to take immediate action." The application can also ask/remind the user to test BS again within an hour or two to ensure that the range is within a tolerable limit.

The application may also send emergency indicators to the user and/or to a medical professional if the blood sugar results are dangerously high or low or have been high or low for an extended period. For example, the indicator may be a text or email message or a flashing screen on the user's device.

The main screen appears after the greeting screen. The exemplary following icons may appear on the main screen, and they may be touch icons or ones that are selected and clicked, or activated in any suitable manner: (1) testing glucose levels; (2) data matrix; (3) location matrix; (4) community tracker; (5) medical professionals; (6) calendar; (7) web application; (8) link to American Diabetic Association; (9) setting; and (10) history option.

The application may learn which aspects a user uses the most and sort icons accordingly from top to bottom.

Figure 35:
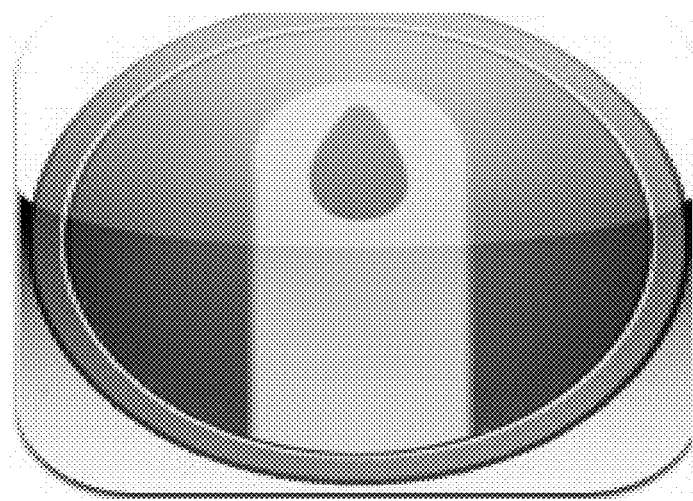
FIG. 35 illustrates an icon in accordance with exemplary embodiments of the disclosure.

Testing:

In this example, where a user's blood sugar level is being measured, the testing apparatus can physically communicate with the computing device, such as by being plugged into it, or may communicate with via any satisfactory wireless method. The icon for testing may look like a finger and blood droplet, as illustrated in FIG. 35.

If the testing apparatus is physically connected (e.g., by a wired connection), it can be placed into an AUX jack on the device (which is shown in FIGS. 14-17). Regardless of how it communicates with the device on which the application is run, a test strip is inserted into the testing apparatus. The light may turn orange on the screen running the application to show that system is calibrating. Once the system has completed calibrating, the light on the screen may turn green/blue and the application screen may show a picture of a blood droplet falling into the top of a test strip. This can appear/flash over and over until blood is applied to the test strip, in order to remind the user to add blood to the test strip.

Next, the user utilizes a lancet to obtain his/her blood sample, which is placed on the test strip. The blood sugar reading will appear on the display screen of the device running the application (e.g., 130 Mg/dl 6/6/2012 at 6:35 PM). Then information about the results may be entered, via the device, such as by a rolling wheel (for a touch screen) displayed by the application. The wheel would allow the user to scroll through a list of items such as: before/after meal; too much food; not enough food; exercise; not enough exercise; carbohydrates; and others (there may be several other options including remarks such as fatty or skinny/chilling at home/on the road; also, large amount of younger adults and children are being diagnosed with Diabetes daily so having options that appeal to a younger demographic could make the application more user friendly).

The application may also include a mapping option that would work with the tracking matrix. For example, after the BS results are shown the application may also store the location of that reading via the device's GPS system (if it has one) which could allow the user to link previously entered data (such as the last meal) to a location on a map. For example: a location (which could be indicated visually by push pins) would be red, which means poor BS. An orange push pin=moderate BS results, and a green push pin=good BS results.

As an example, when the user looks at his map while trying to locate a restaurant, he/she could click on a green push pin location. Once selected the information about that location would be provided, e.g., Vinnie's Pizza Monday 5/20/12 6:35 PM: ½ slice of pizza and a diet coke, BS results 135 Test 1.5 hours after meal. The application could also store a photograph of the location, and using a GPS locator, could identify the results from a prior location or meal by typing in the name of the establishment/meal, the address of the establishment, or using GPS coordinates to identify the establishment.

Tracking Matrix:

The application can utilize meal data and BS results to provide reminders to users of what they ate and the test results for a specific location. The application would notify the user when the GPS recognizes previous locations visited, for example:

The application could display the map and show locations via color-coded push pins or other indictors. The application could load all previous visits to that location, preferably in chronological order, starting with the most recent visit to that location as the first displayed.

The application could show date/time/meal info/photo (optional)/description of the location and meal. This would provide the user a reminder of what they eat and what impact it had on them at the time of testing.

In this manner, the application allows a user to make better decisions about new meals at the same locations. An example of the tracking matrix function follows:

MAP Example A: Spike hill—Williamsburg Brooklyn, N.Y.:
 (a) 5/06/12 9:00 PM 2 slices 1 soda—185 MG/DL-RED.
 (b) 4/30/12 12:45 PM 1 Slice 1 diet soda—156 MG/DL-Orange/Red.
 (c) 4/15/12 3:35 PM 3 slices ½ soda—176 MG/DL-Orange/Red.
 (d) 2/06/12 7:45 PM 1 Slice 1 diet Coke—135 MG/DL-Green.

Thus, when the user enters a location the application will provide the average BS result for that location. Further, it may provide an audio message such as:
 "Johnnie Your Blood Sugar has been above its normal range at this location the past 3 times you eaten here." Or, the screen may turn a color to show the overall impact for the meals a user has eaten at that location, or both.

As time passes and the user completes the meal information while eating and logs test results for different locations the user will have a map that shows locations that promote good diabetic management. Using the GPS functionality of devices and/or stored photographic information, a user may point a device to a restaurant, and results form that restaurant would automatically be displayed.

Viral Community:

The benefit of this feature is to create an environment that allows users to interface with other users on one or more topics, such as: diet; stress control; carbohydrate intake; exercise; medication (side effects and benefits); and provide an open discussion forum. A user could also seek medical professionals to answer questions.

An example of forum queries might be:
 User name: Johnnie Blood—5/5/12 4:55 PM anyone eat kidney beans? If so what effect do they have on your BS?
 User name: Olga Hyper sugar—Yeah, they have a low GI index.
 User Name: Dr. B—yes they are good for your diabetic diet.

Chats may be saved by date with the possibility of linking a chat to GPS so a user has a full history when he/she selects a location to identify a restaurant.

Medical Professionals:

This portion of the application, if used, would allow users to add information about medical professionals, such as: address; contact information; and past results.

A user could set up parameters on the system that the medical professional provides, such as: (a) fasting ranges 88 to 130; and (b) after-meal ranges 120 to 180. Further, a user could provide updates with the medical professional's office. The updates could be provided once weekly or monthly. If the acceptable range of blood sugar level for a user is surpassed the professional is notified (such as via email or text) that the user is over the acceptable range and must set up an appointment.

Calendar:

This portion of the application would allow the user to view information about doctor appointments, meals/locations and BS test results. It also allows the user to visually review the past few days, weeks or months to see how his/her results have been. Graphs and any other visuals would be accessible at this point for a better viewing of their results.

As an example, the user could review the month of June. In this example, during the first three days of the month, the user's BS are within the acceptable BS range. But, on the first weekend of the month, the results are poor. The user could click on each day of the week to see what and where he/she ate. Each day/location will have all previous meal and BS results available for display and the user could review the information on a map or in list results, such as follows:
 6/5/2012—Red
  Mom's house breakfast—9 AM—pancakes, OJ—BS—160—testing 1.5 hrs after meal.
  In-N-Out burger—12:45 PM—double cheeseburger coke and fries—BS 220—testing 2 hours after meal.

Meatball shop—9:30 PM—pasta and meat balls—BS 175—testing 1.5 hours after meal.

The GPS location of each location could be shown in the appropriate color code.

When the user has X number of days "Green" in a row, a congratulation email or pop-up window may be sent to the user.

Settings:

For this function, a user could input medical info/history/records, medicine type into the application, such as: blood pressure; A1C level; cholesterol; carbohydrates; LDL; HDL; triglycerides; abdominal girth; and foot/eye exam results as well as future medical appointments. Further, the user or doctor could add goals so the system or application can gauge results over the course of a given period, such as a day, week or month. As an example: "Johnnie your BS results have been very elevated over the past nine days. Please correct your diet or exercise more." An email could also be sent to medical professionals if the results have been out of range for too long.

The application may also have a child setting so parents can remind a child to enter meal data and test daily. The system could send texts or emails to parents if the child does not test himself within a certain time frame for the day. An alarm may sound if data is not entered within a certain time frame. The application may also be used with seniors as well to ensure that they are entering data into the system within certain time frames.

History of Diabetes:

This would provide a history and up-to-date information about diabetes. The system could load new information to the application, daily, monthly or weekly as it becomes available. The information could include: classification of Diabetes; signs and symptoms; causes; pathology; diagnosis; management; epidemiology; history; society and culture; and references.

Emergency Contact:

The user's emergency contact could be listed on the mobile device and/or computer, for example:

Johnnie R
  Type 1 Diabetic and carry insulin on person 24/7.
  Emergency contact Mandy "The boss" Gagedeen 917 555 5555.

Following are some, non-limiting examples of embodiments according to aspects of the invention that begin with example 1. The examples in this section refer only to other examples in this section and not to the non-limiting examples in other sections.

Example 1: A method performed by a computer program operating on a computer device, the method comprising:
  (a) displaying, by the computer device, on a display screen in communication with the computer device, a plurality of icons related to managing a medical condition;
  (b) receiving, by the computer device, information relating to the medical condition;
  (c) in response to receiving the information, automatically populating, by the computer device, one or more of the plurality of icons with the received information; and
  (d) displaying, by the computer device, the one or more newly populated icons.

Example 2: The method of example 1, wherein the step of receiving information relating to the medical condition comprises:
  (a) receiving, by the computer device, information from an external device in communication with the computer device, wherein the information is relating to the medical condition.

Example 3: The method of example 1 or example 2, further comprising:
  (a) displaying, by the computer device, a blood glucose level of a blood test for a user;
  (b) updating, by the computer device, the blood glucose level in response to a new blood test for the user; and
  (c) in response to the updating of the blood glucose level, displaying, by the computer device, the updated blood glucose level.

Example 4: The method of example 3, further comprising the step of receiving, by the computer device, data for the new blood test from an external device in communication with the computer device.

Example 5: The method of any of examples 1-4, further comprising:
  (a) displaying, by the computer device, a plurality of blood glucose levels for the user, wherein the plurality of blood glucose levels are from past blood tests for the user; and
  (b) displaying, by the computer device, one or more target lines for desired levels of blood glucose.

Example 6: The method of example 5, wherein the steps of displaying further comprise displaying in a color coded display.

Example 7: The method of any of examples 1-6, further comprising displaying, by the computer device, a color coded display for a plurality of pairings of meal data and a blood glucose level for a plurality of geographic locations.

Example 8: The method of any of examples 1-7, wherein one of the plurality of touch icons comprises a glucose level window.

Example 9: The method of any of examples 1-8, wherein one of the plurality of touch icons comprises a glucose tracking window.

Example 10: The method of any of examples 1-9, wherein one of the plurality of touch icons comprises a location update window.

Example 11: The method of any of examples 1-10, wherein one of the plurality of touch icons comprises a community tracker window.

Example 12: The method of any of examples 1-11, wherein one of the plurality of touch icons comprises an activity challenge window.

Example 13: The method of any of examples 1-12, wherein the plurality of touch icons comprises a glucose level window, a glucose tracking window, a location update window, a community tracker window, a calendar window, and an activity challenge window.

Example 14: A tangible non-transitory computer-readable medium having instructions stored thereon that, in response to execution by a computer-based system for managing a medical condition, cause the computer-based system to perform operations comprising:
  (a) displaying, by the computer-based system, on a display screen in communication with the computer-based system, a plurality of touch icons related to managing a medical condition;
  (b) receiving, by the computer-based system, information relating to the medical condition;
  (c) in response to receiving the information, automatically populating, by the computer-based system, one or more of the plurality of touch icons with the received information; and (d) displaying, by the computer-based system, the one or more newly populated touch icons.

Example 15: A system comprising:
(a) a processor for managing a medical condition,
(b) a tangible, non-transitory memory configured to communicate with the processor, the tangible, non-transitory memory having instructions stored thereon that, in response to execution by the processor, cause the processor to perform operations comprising:
  (i) displaying, by the processor, on a display screen in communication with processor, a plurality of touch icons related to managing the medical condition;
  (ii) receiving, by the processor, information relating to the medical condition;
  (iii) in response to receiving the information, automatically populating, by the processor, one or more of the plurality of touch icons with the received information and
  (iv) displaying, by the processor, the one or more newly populated touch icons.

Example 16: The method of any of examples 1-15 wherein the icons are touch icons.

Following are additional, non-limiting examples of embodiments according to aspects of the invention that begin with example 1. The examples in this section refer only to other examples in this section and not to the non-limiting examples in other sections.

Example 1: A kit for testing the level of a substance in bodily fluid, the kit being portable and comprising:
(a) an outer casing having dimensions no greater than 6" in length, 1½" in width and 1½" in depth;
(b) one or more cavities inside of the outer casing, the one or more cavities for retaining one or more devices used for testing the level of a substance in the bodily fluid;
(c) a meter programmed to determine the level of substance in the bodily fluid, the meter positioned in a compartment of the outer housing;
(d) a display that displays the level of the substance in the bodily fluid; and
(e) a port into which bodily fluid is placed so the meter can determine the level of bodily fluid.

Example 2: The kit of example 1 wherein the outer casing is comprised of one or more of plastic and metal.

Example 3: The kit of example 1 or example 2 wherein the outer casing is comprised of urethane.

Example 4: The kit of any of examples 1-3 wherein the outer casing has dimensions no greater than 5" in length, 1" in width and 1½" in depth.

Example 5: The kit of any of examples 1-4 wherein the kit weighs 0.5 lbs. or less.

Example 6: The kit of any of examples 1-5 wherein the kit weighs 0.25 lbs. or less.

Example 7: The kit of any of examples 1-6 that has a plurality of cavities defined within the outer casing and each of the plurality of cavities retains different devices.

Example 8: The kit of example 7 that has two cavities.

Example 9: The kit of example 8 wherein one cavity includes lances and test strips and the other cavity includes needles.

Example 10: The kit of any of examples 7-10 wherein each cavity can be accessed by a hinged door that is closed by being snap fit.

Example 11: The kit of example 1 wherein each of the one or more cavities is accessed by a hinged door that is closed by being snap fit.

Example 12: The kit of any of examples 1-11 wherein the outer casing includes a removable cap.

Example 13: The kit of example 12 wherein at least one cavity is in the removable cap.

Example 14: The kit of any of examples 1-13 wherein the bodily fluid is selected from the group consisting of blood, urine and salvia.

Example 15: The kit of any of examples 1-14 wherein the substance which level is tested is selected from the group consisting of glucose, cholesterol, sodium, potassium, creatine, and protein.

Example 16: The kit of any of examples 1-15 wherein each cavity is accessible by a sliding door.

Example 17: The kit of any of examples 1-16 wherein the meter is a glucose meter.

Example 18: The kit of any of examples 1-17 wherein the display is digital and is part of the meter, the display for displaying the substance level and being visible through the outer casing.

Example 19: The kit of any of examples 1-17 wherein the meter has a digital display that displays the substance level and the outer casing having an opening through which the display can be viewed.

Example 20: The kit of any of examples 1-19 wherein the meter is removable from the compartment in which it is positioned.

Example 21: The kit of any of examples 1-20 wherein the meter is battery powered.

Example 22: The kit of any of examples 1-21 wherein the port extends into the meter.

Example 23: The kit of any of examples 1-22 wherein the meter is activated only when a test strip is positioned in the port.

Example 24: The kit of any of examples 1-22 wherein the meter is activated by an off/on switch accessible through the outer casing.

Example 25: The kit of any of examples 1-24 wherein the port comprises an opening in the outer casing that leads to an opening in the meter.

Example 26: The kit of any of examples 1-25 that includes an insulin pen.

Example 27: The kit of example 26 wherein the insulin pen is positioned and retained in a cavity in the outer casing.

Example 28: The kit of example 27 wherein the insulin pen has a first end that includes an adjustment mechanism that adjusts an amount of insulin to be injected and a second end that receives a needle to inject insulin into a user, wherein outer casing has a first end and a second end, and the adjustment mechanism protrudes from the first end of the outer casing and the second end of the insulin pen protrudes from the second end of the outer casing;
wherein a user can adjust the insulin level, place a needle on the second end of the insulin pen and inject himself/herself without removing the insulin pen from the kit.

Example 29: The kit of any of examples 1-26 that includes a plurality of insulin pens.

Example 30: The kit of any of examples 1-29 that includes a lancet apparatus.

Example 31: The kit of example 30 wherein the lancet apparatus is contained in a second compartment of the outer housing.

Example 32: The kit of example 31 wherein the lancet apparatus is removable from the second compartment.

Example 33: The kit of any of examples 30-32 wherein the lancet apparatus has an end through which a lance extends when the apparatus is activated, and a button to activate the apparatus and extend the lance through the end.

Example 34: The kit of example 33 wherein there is an opening in the outer casing through which the button can be accessed.

Example 35: The kit of any of examples 33-34 wherein the second end of the outer casing has an opening that aligns with the end of the lancet apparatus through which the lance extends when the lancet apparatus is activated, such that the lance extends through the opening in the outer casing when the lancet apparatus is activated.

Example 36: The kit of example 34 or example 35 in which the port is at the second end of the outer housing.

Example 37: The kit of example 36 wherein the port is positioned between the opening in the outer housing through which the lance extends and the second end of the insulin pen.

Example 38: The kit of example 36 wherein the port is positioned above the opening in the outer housing through which the lance extends and the second end of the insulin pen.

Example 39: The kit of example 1 wherein the one or more compartments includes alcohol swabs.

Example 40: The kit of any of examples 1-39 that includes a removable cap that fits over the second end of the casing.

Example 41: The kit of any of examples 1-40 that includes an audio jack to plug into a computing device and transmit information thereto.

Example 42: The kit of any of examples 1-41 that includes a wireless communication device to send and receive data.

Example 43: The kit of any of examples 1-42 that includes a data storage device to store data.

Example 44: The kit of any of examples 1-43 that includes a processor to analyze and organize data.

Example 45: The kit of any of examples 41-44 that includes a data projection screen to project data other than that displayed by the display.

Example 46: The kit of any of examples 1-45 wherein the outer housing is formed in two pieces that can be separated to remove the meter.

Example 47: The system of any of examples 30-35, wherein the portable kit further comprises one or more internal springs disposed in a shaft, wherein the one or more internal springs are positioned to direct the lancet in one direction in the shaft.

Example 48: The system of example 47, wherein one of the internal springs is disposed proximate to the opening in the body assembly, such that the internal spring is positioned to stop the lancet from exiting the body assembly.

Example 49: The system of example 47, wherein one of the internal springs is disposed distal from the opening in the body assembly, such that the internal spring is positioned to project the lancet towards the opening in the body assembly.

Example 50: The system of any of examples 47-49, wherein the portable kit further comprises a trigger connected to the internal frame for starting the projection of the lancet in the shaft.

Example 51: The system of any of examples 47-50, wherein the portable kit further comprises:
(a) an insulin adjustment knob connected to the body assembly; and
(b) an insulin level display window formed in the body assembly.

Following are additional, non-limiting examples of embodiments according to aspects of the invention that begin with example 1. The examples in this section refer only to other examples in this section and not to the non-limiting examples in other sections.

Example 1: A system for testing for a medical condition of a user, the system comprising:
(a) a computer device;
(b) a portable kit in communication with the computer device, the portable kit comprising:
  (i) a body assembly;
  (ii) a lancet;
  (iii) a test strip;
  (iv) an opening formed in the body assembly, wherein the lancet is disposed proximate to the opening;
  (v) a storage area formed in the body assembly, the storage area for storing a plurality of lancets and a plurality of test strips; and
  (vi) wherein the portable kit is configured to read the test strip to determine a level of a bodily fluid for the medical condition.

Example 2: The system of example 1, wherein the portable kit further comprises an auxiliary jack, wherein the auxiliary jack is configured to facilitate communication with the computer device.

Example 3: The system of example 1, wherein the portable kit is configured for wireless communication with the computer device.

Example 4: The system of any of examples 1-3, wherein the portable kit further comprises a digital readout window, wherein the digital readout window displays the determined substance level in the bodily fluid.

Example 5: The system of any of examples 1-4, wherein the portable kit further comprises an indicator light, wherein the indicator light displays a color that is indicative of the determined blood level.

Example 6: The system of any of examples 1-5, wherein the computer device is a smartphone.

Example 7: The system of any of examples 1-6, wherein the determined substance level is a blood glucose.

Example 8: A system for testing for a medical condition of a user, the system comprising:
(a) a computer device;
(b) a portable kit in communication with the computer device, the portable kit comprising:
  (i) a body assembly;
  (ii) a lancet;
(c) a test strip;
(d) an opening formed in the body assembly, wherein the lancet is disposed proximate to the opening;
(e) a storage area formed in the body assembly, for storing a plurality of lancets and a plurality of test strips;
(f) an internal frame having a shaft, wherein the internal frame is connected to the body assembly; and
(g) wherein the portable kit is configured to read the test strip to determine a substance level for a bodily fluid the medical condition.

Example 9: The system of example 8, wherein the portable kit further comprises one or more internal springs disposed in the shaft, wherein the one or more internal springs are positioned to direct the lancet in one direction in the shaft.

Example 10: The system of example 9, wherein one of the internal springs is disposed proximate to the opening in the body assembly, such that the internal spring is positioned to stop the lancet from exiting the body assembly.

Example 11: The system of example 9, wherein one of the internal springs is disposed distal from the opening in the body assembly, such that the internal spring is positioned to project the lancet towards the opening in the body assembly.

Example 12: The system of any of examples 8-11, wherein the portable kit further comprises a trigger connected to the internal frame for starting the projection of the lancet in the shaft.

Example 13: The system of any of examples 8-12, wherein the portable kit further comprises:
(c) an insulin adjustment knob connected to the body assembly; and
(d) an insulin level display window formed in the body assembly.

Example 14: The system of any of examples 8-13, wherein the portable kit is configured for wireless communication with the computer device.

Example 15: The system of any of examples 8-14, wherein the portable kit further comprises a digital readout window, wherein the digital readout window displays the determined blood level.

Example 16: The system of any of examples 8-15, wherein the determined substance level is a blood glucose level.

Example 17: The system of any of examples 8-16, wherein the computer device comprises a smartphone.

Example 18: The system of any of examples 8-17, wherein the portable kit further comprises one or more alcohol swabs, wherein the alcohol swabs are stored in the body assembly.

Example 19: The system of any of examples 8-18, wherein the portable kit further comprises a storage cap for storage of a plurality of lancets.

Example 20: The system of any of examples 8-19, wherein the portable kit further comprises a cover for storage of the portable kit, wherein the cover may be worn on clothing of the user.

Following are additional, non-limiting examples of embodiments according to aspects of the invention that begin with example 1. The examples in this section refer only to other examples in this section and not to the non-limiting examples in other sections.

Example 1: A method performed by a computer program operating on a computer device having a processor and a data storage, the method comprising:
(a) displaying, by the computer device, on a display screen in communication with the computer device, a plurality of icons related to managing a medical condition;
(b) receiving, by the computer device, information relating to the medical condition;
(c) in response to receiving the information, storing in, by the computer device, the data storage with the received information;
(d) selecting, by a user, one of the plurality of icons;
(e) in response to the selection of one of the plurality of icons, launching, by the computer device, an application associated with the icon; and
(f) displaying a result generated by the processor manipulating at least some of the received information.

Example 2: The method of example 1, wherein the step of displaying a result further comprise displaying in a color-coded manner indicative of the nature of the result.

Example 3: The method of example 1 or example 2, wherein one of the plurality of icons functions to display a glucose level.

Example 4: The method of example 3, wherein in response to the selection of the icon that displays the glucose level, the method further comprises:
(a) displaying, by the computer device, a plurality of blood glucose levels for the user; and
(b) displaying, by the computer device, one or more target range lines for the blood glucose levels.

Example 5: The method of example 4, wherein the steps of displaying further comprise displaying in a color-coded display in a manner indicative of the nature of the results.

Example 6: The method of example 4 or example 5, wherein the one or more target range lines comprise a high target range line and a low target range line.

Example 7: The method of example 4, further comprising displaying, by the computer device, information for a plurality of insulin injections for the user.

Example 8: The method of any of examples 4-7, further comprising:
(a) updating, by the computer device, the plurality of blood glucose levels in response to a new blood test for the user; and
(b) in response to the updating of the blood glucose level, displaying, by the computer device, the updated plurality of blood glucose levels.

Example 9: The method of example 8, further comprising the step of receiving, by the computer device, data for the new blood test from an external device in communication with the computer device.

Example 10: The method of example 1, wherein one of the plurality of icons comprises a location update window.

Example 11: The method of example 10, wherein in response to selection of the location update window, the method further comprises:
(a) displaying, by the computer device, a plurality of geographic locations; and
(b) displaying, by the computer device, for each of the plurality of geographic locations, an average blood glucose level for the user.

Example 12: The method of example 11, further comprising displaying, by the computer device, for each of the plurality of geographic locations, meal data for the user.

Example 13: The method of example 11, wherein the steps of displaying further comprise displaying in a color-coded in a manner indicative of the result.

Example 14: The method of any of examples 1-13, wherein one of the plurality of icons comprises a community tracker window.

Example 15: The method of example 14, wherein in response to the selection of the community tracker window, the method further comprises displaying information for the user and for people in a community of the user.

Example 16: The method of any of examples 1-15, wherein one of the plurality of icons comprises an activity challenge window.

Example 17: The method of example 1, wherein the plurality of icons comprises a glucose level window, a glucose tracking window, a location update window, a community tracker window, a calendar window, and an activity challenge window.

Example 18: A tangible non-transitory computer-readable medium having instructions stored thereon that, in response to execution by a computer-based system for managing a medical condition, cause the computer-based system to perform operations comprising:
(a) displaying, by the computer-based system, on a display screen in communication with the computer-based system, a plurality of icons related to managing a medical condition;
(b) receiving, by the computer-based system, information relating to the medical condition;

(c) in response to receiving the information, automatically populating, by the computer-based system, a database with the received information;
(d) receiving, by the computer-based system, a selection by a user of one of the plurality of icons; and
(e) in response to the selection of one of the plurality of icons, launching, by the computer-based system, an application associated with the icon wherein the stored instructions manipulate at least some of the received information in the database.

Example 19: A system comprising:
(a) a processor for managing a medical condition,
(b) a tangible, non-transitory memory configured to communicate with the processor,
(c) the tangible, non-transitory memory having instructions stored thereon that, in response to execution by the processor, cause the processor to perform operations comprising:
  (i) displaying, by the processor, on a display screen in communication with the processor, a plurality of icons related to managing the medical condition;
  (ii) receiving, by the processor, information relating to the medical condition;
  (iii) in response to receiving the information, automatically populating, by the processor, one or more of the plurality of icons with the received information;
  (iv) displaying, by the processor, the one or more newly populated icons;
  (v) receiving, by the processor, a selection of one of the plurality of icons; and
  (vi) in response to the selection of one of the plurality of touch icons, launching, by the processor, an application associated with the icon.

Example 20: The method of any of examples 1-19 wherein each icon is a touch icon.

Example 21: The method of any of examples 1-20 wherein the computer-based system is a smart phone.

Example 22: The method of any of examples 1-20 wherein the computer-based system is a personal computer.

Example 23: The method of any of examples 1-20 wherein the computer-based system is located in a kit according to the invention.

The particular implementations shown and described above are illustrative of the exemplary embodiments and their best mode and are not intended to otherwise limit the scope of the present disclosure in any way. Indeed, for the sake of brevity, conventional data storage, data transmission, and other functional aspects of the systems may not be described in detail. Methods illustrated in the various figures may include more, fewer, or other steps. Additionally, steps may be performed in any suitable order without departing from the scope of the present disclosure. Furthermore, the connecting lines shown in the various figures are intended to represent exemplary functional relationships and/or physical couplings between the various elements. Alternative or additional functional relationships or physical connections may be present in a system according to the claimed inventions.

The term "non-transitory" is to be understood to remove only propagating transitory signals from the claim scope and does not relinquish rights to all standard computer-readable media.

It is contemplated that a method according to aspects of the invention may be embodied as computer program instructions on a tangible computer-readable carrier, such as a magnetic or optical memory or a magnetic or optical disk.

What is claimed is:

1. A method performed by a computer program operating on a computer device that is a smartphone, the method comprising:
(a) displaying, by the computer device, on a display screen in communication with the computer device, a plurality of icons related to managing a medical condition, wherein one of the plurality of icons comprises a community tracker window which, upon selection by the user, shows the activity of other people in a community of which the user is a member, including a leaderboard showing points earned and lost by the user and other people in the user's community, the point associated with blood glucose levels of the user and other people in the user's community, and wherein one of the plurality of icons comprises an activity challenge window which, upon selection by the user, displays a periodically updated activity to challenge the user;
(b) receiving, by the computer device, information relating to the medical condition;
(c) in response to receiving the information, automatically populating, by the computer device, one or more of the plurality of icons with the received information;
(d) displaying, by the computer device, the one or more newly populated icons;
(e) displaying, by the computer device, a color coded display for a plurality of pairings of meal data and a blood glucose level for a plurality of geographic locations;
(f) acquiring, by a digital camera of the computer device, a digital image of a street at the current physical location of the smartphone, the digital image of the street having a first restaurant and a second restaurant visible in the digital image;
(g) calculating, by the computer device, an average blood sugar level of the user at the first restaurant and an average blood sugar level of the user at the second restaurant;
(h) modifying, by the computer device, the digital image of the street a first time by inserting the average blood sugar of the user at the first restaurant onto a portion of the digital image of the street occupied by the first restaurant;
(i) modifying, by the computer device, the digital image of the street a second time by inserting the average blood sugar of the user at the second restaurant onto a portion of the digital image of the street occupied by the second restaurant; and
(j) displaying, on the display screen, the modified digital image of the street to allow the user to view the users average blood sugar results at the first restaurant and the second restaurant.

2. The method of claim 1, wherein the step of receiving information relating to the medical condition comprises:
(a) receiving, by the computer device, information from an external device in communication with the computer device, wherein the information is relating to the medical condition.

3. The method of claim 1, further comprising:
(a) displaying, by the computer device, a blood glucose level of a blood test for a user;
(b) updating, by the computer device, the blood glucose level in response to a new blood test for the user; and
(c) in response to the updating of the blood glucose level, displaying, by the computer device, the updated blood glucose level.

4. The method of claim 3, further comprising the step of receiving, by the computer device, data for the new blood test from an external device in communication with the computer device.

5. The method of claim 1, further comprising:
   (a) displaying, by the computer device, a plurality of blood glucose levels for the user, wherein the plurality of blood glucose levels are from past blood tests for the user; and
   (b) displaying, by the computer device, one or more target lines for desired levels of blood glucose.

6. The method of claim 1, wherein one of the plurality of icons comprises a glucose tracking window.

7. The method of claim 1, wherein one of the plurality of icons comprises a location update window which, upon selection by the user, shows the user's average glucose level at various restaurants previously visited by the user.

8. The method of claim 7, further comprising displaying, on the display screen, and responsive to the user entering a restaurant displayed on the location update window where the user's average glucose level was high, a colored background to alert the user of past poor diabetic management associated with the restaurant.

9. The method of claim 1, further comprising:
   (f) displaying, on the display screen, an image acquired from a camera of the computer device; and
   (g) annotating, on the displayed image, a location associated with one of the plurality of pairings of meal data and a blood glucose level.

10. The method of claim 8, wherein the colored background is red.

11. A method performed by a computer program operating on a computer device, the method comprising:
    (a) displaying, by the computer device, on a display screen in communication with the computer device, a plurality of icons related to managing a medical condition, wherein one of the plurality of icons comprises a community tracker window which, upon selection by the user, shows the activity of other people in a community of which the user is a member, including a leaderboard showing points earned and lost by the user and other people in the user's community, the point associated with blood glucose levels of the user and other people in the user's community, and wherein one of the plurality of icons comprises an activity challenge window which, upon selection by the user, displays a periodically updated activity to challenge the user;
    (b) receiving, by the computer device, information relating to the medical condition;
    (c) in response to receiving the information, automatically populating, by the computer device, one or more of the plurality of icons with the received information;
    (d) displaying, by the computer device, the one or more newly populated icons;
    (e) displaying, by the computer device, a color coded display for a plurality of pairings of meal data and a blood glucose level for a plurality of geographic locations;
    (f) wherein one of the plurality of icons comprises a location update window which, upon selection by the user, shows the user's average glucose level at various restaurants previously visited by the user; and
    (g) displaying, on the display screen, and responsive to the user entering a restaurant displayed on the location update window where the user's average glucose level was high, a colored background to alert the user of past poor diabetic management associated with the restaurant.

12. The method of claim 11, wherein the step of receiving information relating to the medical condition comprises:
    (a) receiving, by the computer device, information from an external device in communication with the computer device, wherein the information is relating to the medical condition.

13. The method of claim 11, further comprising:
    (a) displaying, by the computer device, a blood glucose level of a blood test for a user;
    (b) updating, by the computer device, the blood glucose level in response to a new blood test for the user; and
    (c) in response to the updating of the blood glucose level, displaying, by the computer device, the updated blood glucose level.

14. The method of claim 13, further comprising the step of receiving, by the computer device, data for the new blood test from an external device in communication with the computer device.

15. The method of claim 11, further comprising:
    (a) displaying, by the computer device, a plurality of blood glucose levels for the user, wherein the plurality of blood glucose levels are from past blood tests for the user; and
    (b) displaying, by the computer device, one or more target lines for desired levels of blood glucose.

16. The method of claim 11, wherein the computer device is a smartphone.

17. The method of claim 11, wherein one of the plurality of icons comprises a glucose tracking window.

18. The method of claim 11, further comprising:
    (a) displaying, on the display screen, an image acquired from a camera of the computer device; and
    (b) annotating, on the displayed image, a location associated with one of the plurality of pairings of meal data and a blood glucose level.

19. The method of claim 11, wherein the colored background is red.

* * * * *